US012656000B2

(12) United States Patent
Knight et al.

(10) Patent No.: US 12,656,000 B2
(45) Date of Patent: Jun. 16, 2026

(54) DISINFECTION HUMIDIFIER AND METHODS USING THE SAME

(71) Applicant: SOCLEAN, INC., Peterborough, NH (US)

(72) Inventors: James Knight, Bedford, NH (US); Robert Wilkins, Peterborough, NH (US); Kelly Graham, Peterborough, NH (US); Charles Robert, New Boston, NH (US); Tahira Jayasuriya, Peterborough, NH (US)

(73) Assignee: SOCLEAN, INC., Peterborough, NH (US)

(*) Notice: Subject to any disclaimer, the term of this patent is extended or adjusted under 35 U.S.C. 154(b) by 343 days.

(21) Appl. No.: 18/369,608

(22) Filed: Sep. 18, 2023

(65) Prior Publication Data

US 2024/0003558 A1 Jan. 4, 2024

Related U.S. Application Data

(63) Continuation of application No. PCT/US2022/071198, filed on Mar. 17, 2022.

(Continued)

(51) Int. Cl.
*F24F 6/04* (2006.01)
*A61L 2/202* (2026.01)
(Continued)

(52) U.S. Cl.
CPC .............. *F24F 6/043* (2013.01); *A61L 2/202* (2013.01); *B01F 23/215* (2022.01); *F24F 3/14* (2013.01); *F24F 8/26* (2021.01); *F24F 2006/046* (2013.01)

(58) Field of Classification Search
CPC ............ F24F 3/14; B01F 23/21; B01F 23/215
See application file for complete search history.

(56) References Cited

U.S. PATENT DOCUMENTS 2,265,252 A 12/1941 Schaefer
2,678,235 A 5/1954 Perlman
(Continued)

FOREIGN PATENT DOCUMENTS

CA 2221944 C 4/2004
CA 2549359 C 1/2012
(Continued)

OTHER PUBLICATIONS

International Search Report and Written Opinion from corresponding PCT Appln. No. PCT/US22/71198, dated Aug. 17, 2022. 14 pages.

*Primary Examiner* — Robert A Hopkins
(74) *Attorney, Agent, or Firm* — Secant IP, P.L.L.C.

(57) ABSTRACT

A humidifier includes a housing, a water reservoir configured to hold a quantity of water, a fan assembly configured to generate an air flow path within the humidifier, a sanitizing system, and a wick assembly. The sanitizing system is configured to generate a sanitizing gas and to transfer the sanitizing gas to the water reservoir such that at least a portion of the sanitizing gas is absorbed into the water in the water reservoir. The wick assembly is fluidly configured to receive water from the water reservoir and transfer the water into the air flow path to generate humidified air. The water received by the wick assembly includes at least a portion of the sanitizing gas absorbed into the water, wherein at least a portion of the water received by wick assembly flows back to the water reservoir.

17 Claims, 22 Drawing Sheets

Related U.S. Application Data

(60) Provisional application No. 63/200,604, filed on Mar. 17, 2021, provisional application No. 63/200,607, filed on Mar. 17, 2021.

(51) Int. Cl.
B01F 23/21 (2022.01)
F24F 3/14 (2006.01)
F24F 8/26 (2021.01)

(56) References Cited

U.S. PATENT DOCUMENTS

| | | | |
|---|---|---|---|
| 4,089,915 A | | 5/1978 | Jackson |
| 5,143,655 A | | 9/1992 | Chiu et al. |
| 5,677,982 A | | 10/1997 | Levine et al. |
| 5,975,502 A | * | 11/1999 | Stanek .................... F24F 6/043 |
| | | | 261/36.1 |
| 6,845,971 B2 | | 1/2005 | Bachert |
| 7,338,358 B2 | | 3/2008 | Kim et al. |
| 7,854,900 B2 | | 12/2010 | Takeda et al. |
| 8,354,057 B2 | | 1/2013 | Heselton et al. |
| 8,940,085 B2 | | 1/2015 | Markham et al. |
| 9,011,787 B2 | | 4/2015 | Dunkley et al. |
| 9,482,440 B2 | | 11/2016 | Markham et al. |
| 2008/0073204 A1 | | 3/2008 | Kobayashi et al. |
| 2011/0076186 A1 | | 3/2011 | Itzhak et al. |
| 2013/0154131 A1 | | 6/2013 | Hou |
| 2013/0175711 A1 | | 7/2013 | Nutter et al. |
| 2017/0038083 A1 | | 2/2017 | Markham et al. |
| 2017/0224857 A1 | | 8/2017 | Leyva et al. |
| 2018/0172299 A1 | | 6/2018 | Conrad |

FOREIGN PATENT DOCUMENTS

| | | | | | |
|---|---|---|---|---|---|
| CN | 2220033 Y | * | 2/1996 | | |
| CN | 2646601 Y | | 10/2004 | | |
| CN | 2710637 Y | | 7/2005 | | |
| CN | 201147215 Y | | 11/2008 | | |
| EP | 3647671 A1 | | 5/2020 | | |
| JP | 4740080 B2 | | 8/2011 | | |
| KR | 200178082 Y1 | | 4/2000 | | |
| KR | 100550382 B1 | | 3/2006 | | |
| TW | 201247253 A | | 12/2012 | | |
| WO | WO-2009070902 A1 | * | 6/2009 | .............. | F24F 6/043 |

* cited by examiner

10

24

12

20

18

14

16

22

18

18

300

DISINFECTION HUMIDIFIER AND METHODS USING THE SAME

CROSS REFERENCE TO RELATED PATENT APPLICATION

This application is a continuation of International application No. PCT/US22/71198 filed Mar. 17, 2022, which is based on and claims the benefit of U.S. Provisional Patent Application No. 63/200,604, filed, Mar. 17, 2021, and U.S. Provisional Patent Application No. 63/200,607, filed Mar. 17, 2021, beth all of which are incorporated by reference herein in their entirety.

TECHNICAL FIELD

The present disclosure generally relates to technologies for sanitizing humidifiers. More specifically, the present disclosure relates to technologies for sanitizing a humidifier with a sanitizing gas. Devices, systems, and methods using such technologies are also disclosed.

BACKGROUND INFORMATION

Many humidifiers (e.g., cool and warm mist humidifiers) have a reservoir and a base tray. The reservoir is generally configured to store and release water into the base tray. The water may be used to produce humidified air in several different ways, depending on the configuration of the humidifier. In a wick humidifier, water in a base tray is drawn into a wick (e.g., an adsorbent or absorbent mat), after which at least some of the water is transferred into the surrounding air. For example, a fan in a wick humidifier may cause air to flow over the mat. The air flow may cause at least a portion of the water in the mat to evaporate into the surrounding air, producing humidified air. The humidified air may then be conveyed out of the humidifier into the surrounding environment in any suitable manner.

The liquid reservoir, base tray, and other passageways within a humidifier are often warm, moist, and dark. Consequently, such components (and particularly the surfaces thereof) often become fouled with bacteria, mold and other contaminants. Use of the humidifier when it is fouled with such contaminants can present a health issue, as the bacteria, mold, etc. may be conveyed into the surrounding environment by the humidified air generated by the humidifier.

To avoid such issues, users generally need to manually clean the reservoir, base tray, and other components of a humidifier. Many users, however, find cleaning a humidifier to be difficult, messy, and/or inconvenient. Consequently, many users forego cleaning a humidifier, particularly when components that are fouled with bacteria are hidden from view, and/or when the contamination is not easily identified. Moreover, some parts/passageways of a humidifier may be difficult for a user to access—making effective manual cleaning difficult or impossible.

In addition to being difficult and/or inconvenient to clean, many modern humidifiers use a "bottom filling" reservoir—i.e., a reservoir that includes a water inlet on the bottom thereof. To fill such a reservoir, a user generally needs to remove the reservoir from a base of the humidifier, invert the base so that the inlet is facing upwards, unscrew a fill cap over the inlet, fill the reservoir, replace the screw cap, invert the reservoir again so that the inlet is facing downwards, and replace the reservoir in the base of the humidifier. That process can be messy, inconvenient, and present point of failure for many users (e.g., when a user inadequately secures the fill cap after the reservoir is filled). Moreover, when the reservoir is fouled with bacteria, inversion of the reservoir during filling may disturb bacterial growth on the sidewalls of the reservoir. This may disperse bacteria or other contaminants in the water within the reservoir and facilitate the incorporation and distribution of bacteria/contaminants with the humidifier air produced by the humidifier.

Accordingly, the inventors have identified that there is a continued interest in the development of novel devices, systems, and methods for cleaning, sanitizing and disinfecting all or a portion of a humidifier.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

FIG. 7 is another cross-sectional top view of the wick cartridge of FIG. 4, consistent with the present disclosure.

DETAILED DESCRIPTION

Figure 1:
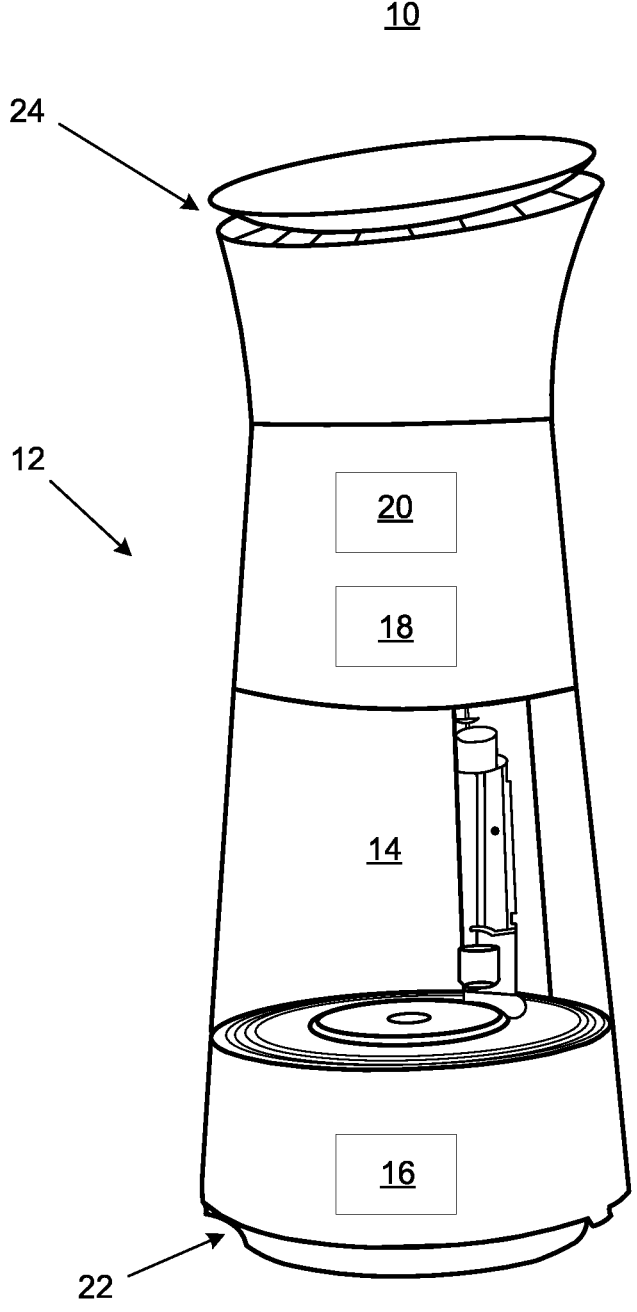
FIG. 1 is a block diagram of one example of a humidifier, consistent with the present disclosure.

Turning to FIG. 1, a block diagram of one example of a humidifier 10 is generally illustrated. The humidifier 10 may include a housing 12, one or more water reservoirs 14, one or more fan assemblies 16, one or more wick assemblies 18, and one or more sanitizing systems 20. As explained herein, air may be drawn into the humidifier 10 by the fan assembly 16, for example, through one or more grills 22. Water from the water reservoir 14 is evaporated into the air drawn into the humidifier 10 by the wick assemble 18, and the humidified air is conveyed out of a humidified air outlet 24 of the humidifier 10 by the fan assembly 16 into the surrounding environment. The sanitizing system 20 is configured to prevent and/or reduce the growth of bacteria, mold, and/or virus within all or a portion of the humidifier 10. In at least one example, the sanitizing system 20 is configured to prevent and/or reduce the growth of bacteria, mold, and/or virus within the water reservoir 14, the wick assembly 18, and/or the humidified air outlet 24. In at least one example, the sanitizing system 20 may utilize ozone to sanitize the humidifier 10.

Figure 2:
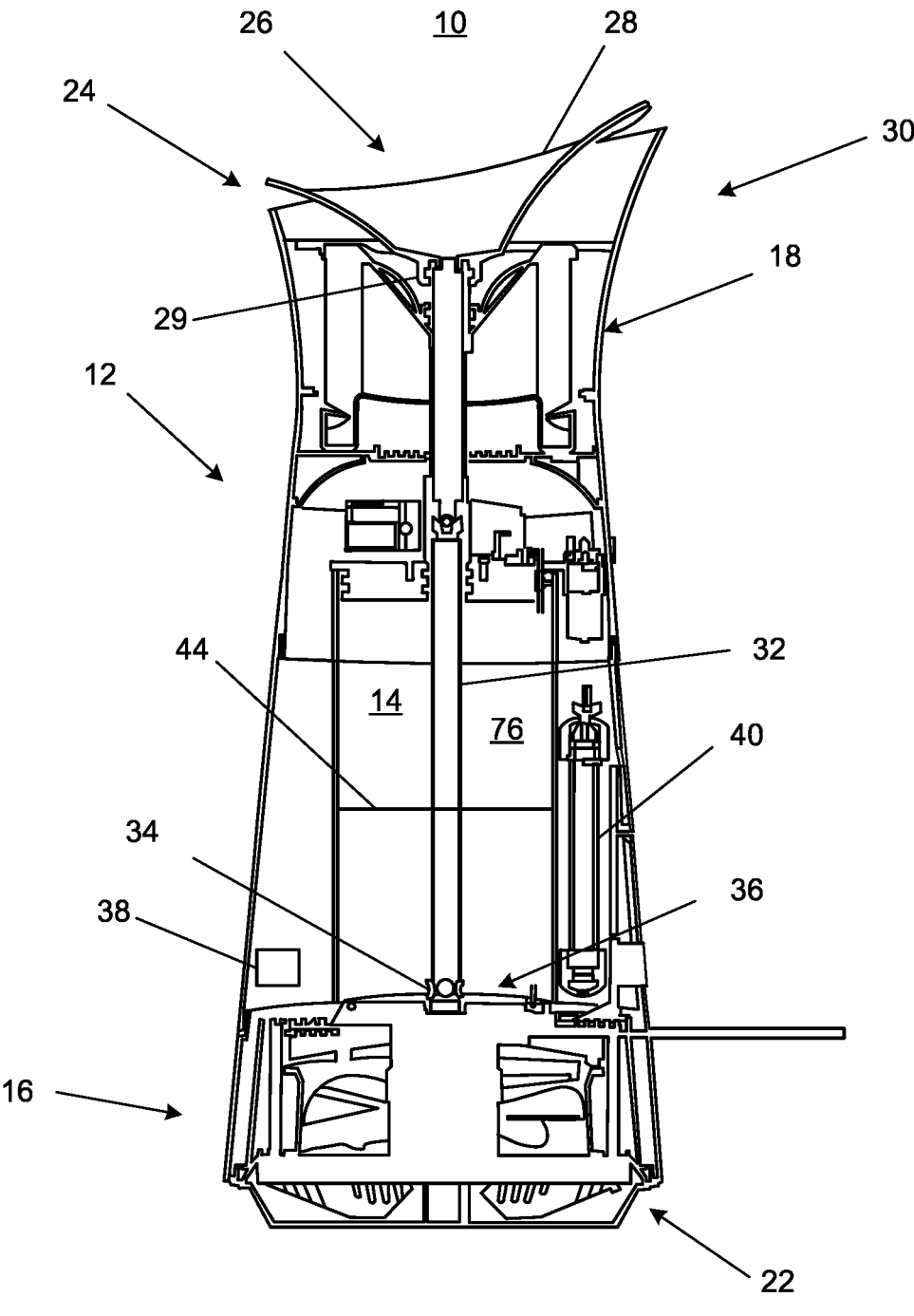
FIG. 2 is a cross-sectional view of one example of the humidifier of FIG. 1, consistent with the present disclosure.

With reference to FIG. 2, a cross-sectional view of one example of the humidifier 10 of FIG. 1 is generally illustrated. The humidifier 10 may include a water inlet 26 in fluid communication with the water reservoir 14. In at least one example, the water inlet 26 may include a funnel 28 disposed proximate the top 30 of the humidifier 10. The funnel 28 provides an easy way for a user to add water to the water reservoir 14 without having to remove the water reservoir 14 as is common in many other designs. The funnel 28 may be fluidly coupled to the water reservoir 14 by one or more water inlet tubes 32. One or more valves 29 (e.g., one-way flow valves such as check valves or the like) may be provided to generally prevent water from flowing from the water reservoir 14 up the water inlet tube 32, e.g., in the event the humidifier is tipped over.

The distal or bottom end of the water inlet tube 32 may include one or more outlets 34 disposed proximate the bottom or base 36 of the water reservoir 14. The outlet 34 may be arranged such that it is generally always submerged under the water within the water reservoir 14 such that gas (e.g., ozone) in the headspace above the water within the water reservoir 14 generally cannot enter into the water inlet tube 32 (i.e., without being absorbed by the water in the water reservoir 14). In some examples, one or more water level sensors 38 may be provided. The water level sensors 38 may generate a signal representative of the water level in the water reservoir 14 and may include any known sensor for detecting the water level 44 within the water reservoir 14. A non-exhaustive list of water level sensors 38 includes contact sensors, ultrasonic sensors, capacitive sensors, pressure sensors, radar level sensors, and the like.

The sanitizing system 20 may receive the signal from the water level sensors 38 and adjust various parameters based on this signal. For example, the sanitizing system 20 may stop and/or prevent ozone from being introduced into the water reservoir 14 if the water level within the water reservoir 14 is too low. Additionally (or alternatively), the sanitizing system 20 may cause gas (e.g., ozone) within the headspace above the water in the water reservoir 14 to flow through one or more filters 40. The filters 40 may be in fluid communication with the headspace in the water reservoir 14, and may include filters configured to remove all or a portion of the sanitizing gas (e.g., ozone) by converting the sanitizing gas (e.g., ozone) into a breathable gas (e.g., oxygen). The resulting filtered headspace airstream may then be directed out of the device, e.g., via a discharge outlet. For example, when the sanitizing gas is ozone, filter assembly 40 may include a conversion media that is configured to convert at least a portion of the ozone in the headspace airstream to oxygen. Non-limiting examples of materials that may be used as such filter media include activated carbon, magnesium oxide, magnesium dioxide, manganese dioxide, zeolite, combinations thereof or the like, all of which can facilitate the conversion of ozone to oxygen.

Figure 3:
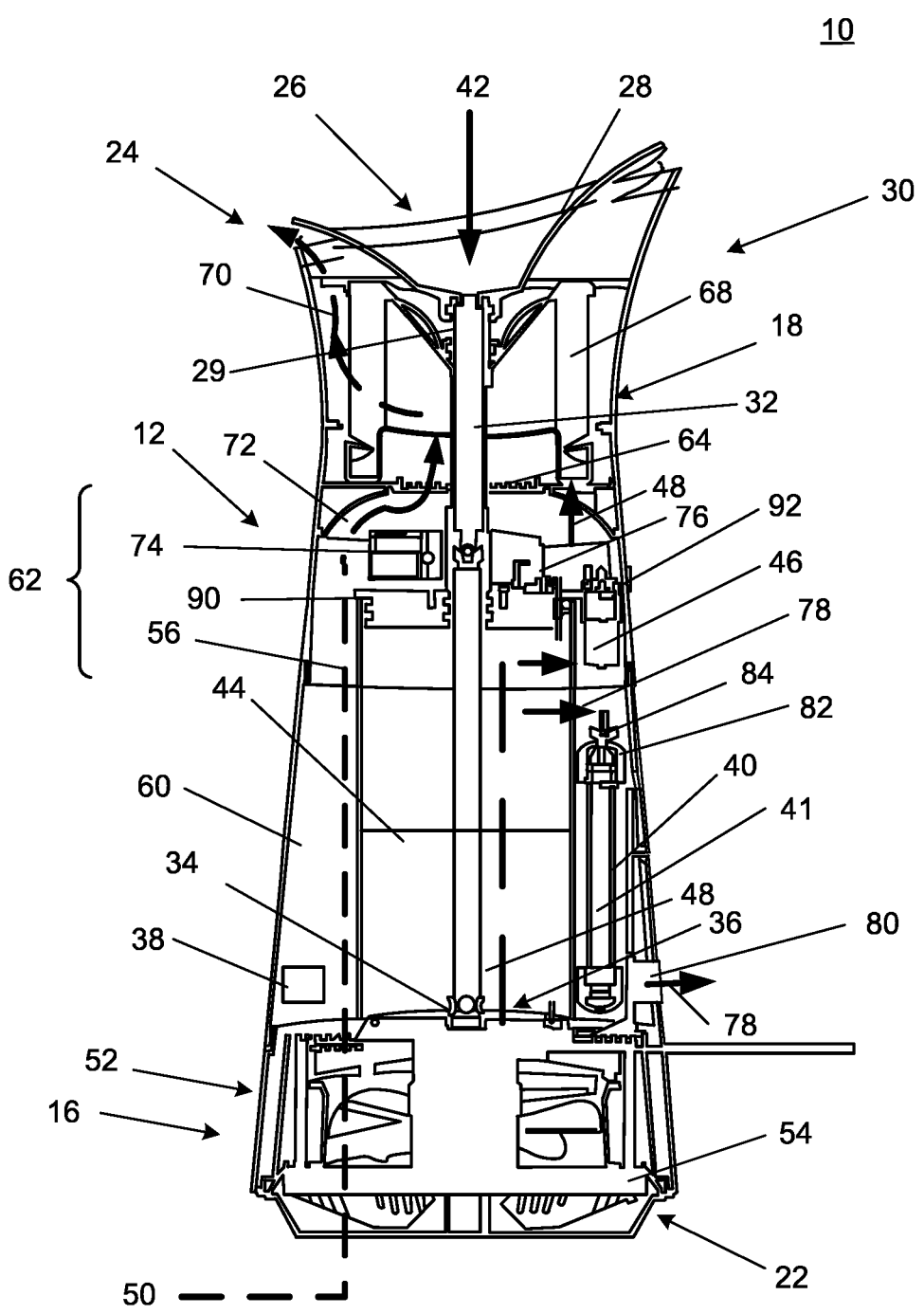
FIG. 3 is a cross-sectional view of the humidifier of FIG. 2 generally illustrated including various flow paths, consistent with the present disclosure.

Turning now to FIG. 3, a cross-sectional view of the humidifier 10 of FIG. 2 is generally illustrated including various flow paths. Water 42 may be introduced into the water reservoir 14 using the funnel 28 and the water inlet tube 32 such that the water level 44 within the water reservoir 14 is above a minimum threshold, e.g., as set by the water level sensor 38. At least a portion of the water reservoir 14 may be formed by a transparent or semi-transparent material to allow a user to see the water level 44. The humidifier 10 may also include one or more water pumps 46 fluidly coupled to the water reservoir and to the wick assemble 18, e.g., as generally illustrated by supply water lines 48. Optionally, the humidifier 10 may include a return water lines (not shown for clarity). In at least example, the return water lines may be configured to allow excess water to flow from the wick assemble 18 back to the water reservoir 14. The water pump 46 may be disposed above the water reservoir 14, and in at least one example, the water pump 46 includes a diaphragm water pump (though the present disclosure is not limited to this unless specifically claimed as such).

The humidifier 10 may also include an air flow path. In particular, environmental air 50 may be drawn into the humidifier 10 by the fan assembly 16, for example, through one or more grills 22. The fan assembly 16 and/or the grills 22 may be located proximate to the lower housing or base 52, though it should be appreciated that the fan assembly 16 and/or the grills 22 may be located anywhere in the humidifier 10. Optionally, one or more air filters 54 (such as, but not limited to, high-efficiency particulate air (HEPA) filters or the like) may be provided either before and/or after the fan assembly 16 to remove at least some of the particulates in the environmental air 50. The fan assembly 16 may include any known air fan configured to cause an air flow. By way of a non-limiting example, the fan assembly 16 may include one or more electric motors coupled to one or more fan blades as shown.

The supply air 56 (e.g., environmental air 50 and/or filtered environmental air downstream which has not had its humidity level increased) may flow from the fan assembly 16 to the wick assembly 18. In at least one example, the supply air 56 may be configured to flow within the housing 12 at least partially around the water reservoir 14. For example, the water reservoir 14 may be arranged in a central region of a generally of the housing 12 such that the supply air 56 flows generally concentrically around the water reservoir 14 (e.g., around at least 80% of the water reservoir 14). In at least one example, the housing 12 may include a transparent or semitransparent window 58. The at least partially transparent window 58 may be arranged to allow a user to see the water level 44 within water reservoir 14. The window 58 and the water reservoir 14 may at least partially define a supply air passageway 60 within the humidifier 10 for the supply air 56. Optionally, the supply air 56 may flow around at least a portion of the sanitizing system 20 and/or water pump 46. The supply air 56 flowing around the sanitizing system 20 and/or water pump 46 may remove heat from these components, thus increasing their operating lifespan.

The housing 12 (e.g., the upper portion 62) may include/define a supply air inlet 64 configured to allow the supply air 56 to flow into a wick air cavity 66 (which is at least partially defined by the wick assembly 18, including the wick 68). For example, the housing 12 (e.g., the upper portion 62 of the housing 12) may include a radiused or tapered cap 72 which at least partially defines the supply air inlet 64. The tapered cap/funnel 72 may facilitate the supply air 56 flowing from the supply air passageway 60 to the wick air cavity 66. In at least one example, the water inlet tube 32 may extend through the wick assembly 18 (e.g., through the wick air cavity 66) and the supply air inlet 64. For example, the water inlet tube 32 may be aligned coaxially with the wick air cavity 66, the supply air inlet 64, and/or the water reservoir 14.

Once the supply air 56 flows into the wick air cavity 66, at least some of the supply air 56 flows through and/or over the wick 68. As the supply air 56 contacts the wick 68, water pumped by the water pump 48 from the water reservoir 14 is transferred (e.g., evaporated) from the wick 68 into the supply air 56 to create humidified air 70. In at least one embodiment, the wick 66 may be secured within and/or sealed to the wick assembly 18 such that the supply air 56 can only flow through the wick 66. In any rate, the humidified air 70 exits the humidifier for example, through one or more humidified air outlet 24.

The sanitizing system 20 is configured to generate a sanitizing gas to prevent and/or reduce the growth of bacteria, mold, and/or virus within all or a portion of the humidifier 10 (e.g., the water reservoir 14, the wick assembly 18, and/or the humidified air outlet 24). For example, the sanitizing system 20 may include one or more ozone generators 74 and optionally one or more air pumps 76. In particular, the ozone generators 74 may be configured to generate ozone gas, and the air pumps 76 may be configured cause the ozone gas to flow from the ozone generators 74 to the water reservoir 14. The air pumps 76 may be further configured to cause the ozone gas to be dispensed/distributed directly into the water within the water reservoir 14 (e.g., in the form of ozone bubbles). The ozone bubbles may be selected such that a sufficient amount of ozone is absorbed into the water within the water reservoir 14. As a result, the water that is pumped from the water reservoir 14 to the wick assembly 18 (e.g., by water pump 46) may also include absorbed ozone. The absorbed ozone in the water may be at a sufficient level to prevent and/or reduce the growth of bacteria, mold, and/or virus within all or a portion of the humidifier 10 (e.g., the water reservoir 14, the wick assembly 18, and/or the humidified air outlet 24).

Figure 11:
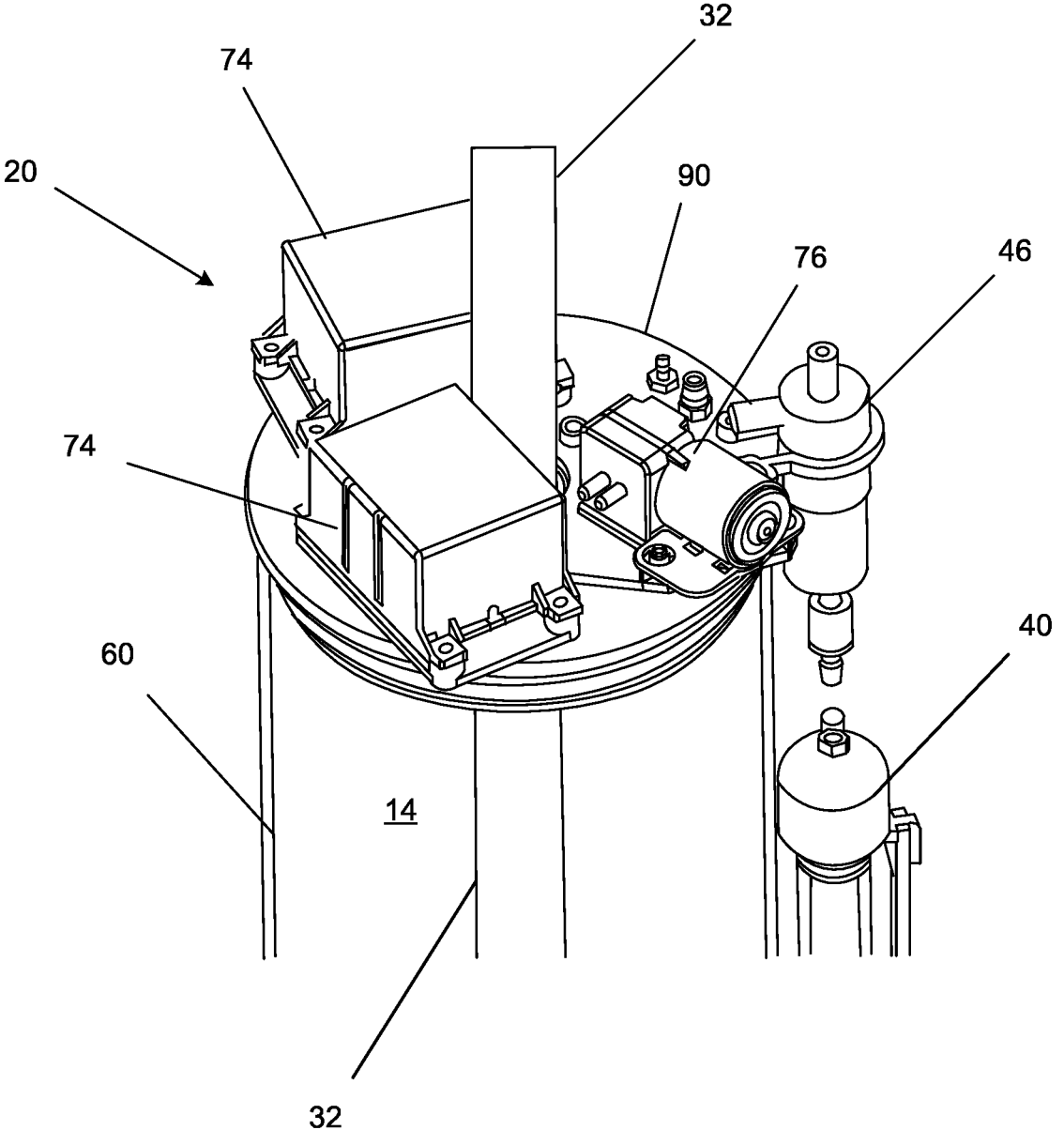
FIG. 11 is a block diagram of one example of a sanitizing system, water pump, controller, and filter assembly, consistent with the present disclosure.

In at least one example (e.g., generally illustrated in FIG. 11), the sanitizing system 20 includes two ozone generators 74 having an output of approximately 500-800 ppm ozone concentration in the air flow, though it should be appreciated that the concentration of ozone may be selected based on the size of the water reservoir 14 and/or the wick assembly 18, as well as the desired ozone concentration ramp up time and holding time period. By way of a non-limiting example, the sanitizing system 20 may be configured to cause an ozone concentration in the water within the water reservoir 14 of at least 0.2 ppm, for example, greater than 0.3 ppm, and/or in the range of 0.2-0.4 ppm. The sanitizing system 20 may also be configured to hold these ozone concentration levels in the water in the water reservoir 14 for 10 minutes or more, for example, 15 minutes or more, 10-25 minutes, and/or 15 minutes (including all ranges and values therein). The ramp up time for the ozone concentration may be approximately 5-25 minutes, for example, 1020 minutes and/or 15 minutes (including all ranges and values therein). It should be appreciated that the sanitizing system 20 may run for a predefined amount of time. For example, the sanitizing system 20 may operate for a predetermined amount of time after the humidifier 10 is turned on. The sanitizing system 20 may operate for periodically and/or each time water is added to the water reservoir 14. Alternatively, the sanitizing system 20 may operate continuously while the humidifier 10 is turned on.

With reference back to FIG. 3, ozone that is not absorbed by the water within the water reservoir 14 may collect in the headspace 76 above the water 44. A filter assembly 40 may be fluidly coupled between the headspace 76 and the environment, for example, to remove excess ozone gas within the headspace 76. The filter assembly 40 may include a conversion media/filter 41 that is configured to convert at least a portion of the ozone in the headspace 76 airstream to oxygen, which may exit the humidifier 10 through one or more evacuation ports 80. Non-limiting examples of materials that may be used as such filter media 41 include activated carbon, magnesium oxide, magnesium dioxide, manganese dioxide, zeolite, combinations thereof or the like, all of which can facilitate the conversion of ozone to oxygen. In at least one example, the filter assembly 40 is always fluidly coupled to the headspace 76 such that environmental air may be drawn into the headspace 76 as the water level 44 within the reservoir 14 drops, and gas within the headspace 76 may be removed from the headspace 76 as the water level 44 within the reservoir 14 increases.

Optionally, an air pump may be provided that is configured to generate an evacuation air flow 78 to remove gas (e.g., ozone gas) within the headspace 76 and cause the gas to flow through the filter assembly 40. The air pump may be the same as the air pump 76 used in the sanitizing system 20. Alternatively, the filter assembly 40 may include a separate air pump. The filter assembly 40 may also optionally include one or more air valves 82 configured to selectively open/close the fluid pathway of the filter assembly 40. For example, the air valve 82 may be configured to generally seal the headspace 76 from the evacuation port 80 and/or the filter media when the humidifier 10 is performing a sanitization process. At the end of the sanitization process (or any other event in which the sanitizing gas within the headspace 76 needs to be removed), the air valve 82 may fluidly couple the headspace 76 to and the filter media and the evacuation port 80. Optionally, the filter assembly 40 may include a water valve 84 configured to generally prevent water (including water vapor) from entering into the filter media 41. As may be appreciated, the efficiency of the filter media 41 may decrease due to water contamination. The water valve 84 may generally prevent and/or reduce water contamination of the filter media 41. In at least one example, the water valve 41 may include a PTFE barrier configured to allow gas (include ozone gas) to flow through, while generally preventing water (including water vapor) from flowing through to the filter media 41. Alternatively (or in addition), the filter assembly 40 may include a heating element to prevent and/or remove water buildup in the filter assembly 40 (an in particular, in the filter media 41).

The humidifier 10 may optionally include one or more controllers 90 and/or user interfaces 92 configured to control the operations of fan assemblies 16, wick assemblies 18, and/or one or more sanitizing systems 20. Controller 90 is generally configured to control the operation of the humidifier 10, e.g., during the performance of humidification operations and termination operations described herein. User interface 92 is generally configured to enable a user to initiate performance of a humidification operations and/or disinfection operations, and/or to terminate humidification operations and/or disinfection operations that are currently in process. For example, user interface may include one or more buttons, switches, or other interactive elements that allow a user to initiate humidification operations and/or disinfection operations. In response to an input from a user, the user interface 92 may produce and send an initiation signal to controller 90. In response to the initiation signal, the controller 90 may initiate the performance of humidification operations and/or disinfection operations.

For example, the controller 90 may be configured to control the operation of the fan assembly 16, e.g., to increase, decrease, start, and/or stop the flow of air through the humidifier 10. The controller 90 may adjust the operating parameters of the fan assembly 16 based on one or more user selections and/or sensors (e.g., humidity and/or temperature sensors). Alternatively (or in addition), the controller 90 may be configured to control the operation of the wick assembly 18. For example, the controller 90 may be configured to increase or decrease the water level within the wick assembly 18 (e.g., based on one or more water sensors associated with the wick assembly 18) and/or adjust the operation of the sanitizing system 20 based on sensors in the wick assembly 18 (e.g., based on one or more debris sensors, ozone concentration sensors, and/or air flow sensors associated with the wick assembly 18).

Alternatively (or in addition), the controller 90 may be configured to control the operation of the sanitizing system 20. For example, the controller 90 may be configured to start sanitizing operations (e.g., ozone generation), stop sanitizing operations (e.g., ozone generation), increase and/or decrease the ozone concentration within the water reservoir 14 and/or wick assembly 18 (e.g., based on one or more debris sensors, ozone concentration sensors, and/or air flow sensors associated with the water reservoir 15 and/or wick assembly 18) as generally described herein. The controller 90 may include a timer to automatically start/stop the operation of the sanitizing system 20.

Controller 90 can include one or more processor(s) and one or more memory device(s). The processor(s) of controller 90 can be any suitable processing device, such as a microprocessor, microcontroller, integrated circuit, or other suitable processing device. The memory device(s) of controller 90 can include any suitable computing system or media, including, but not limited to, non-transitory computer-readable media, RAM, ROM, hard drives, flash drives, or other memory devices. The memory device(s) of controller 90 can store information accessible by the processor(s) of controller 90 including instructions that can be executed by the processor(s) of controller 90 in order to execute various humidification and/or sanitizing operations or cycles. Controller 90 is communicatively coupled with various operational components of the humidifier 10, such as components of fan assemblies 16, wick assemblies 18, and/or one or more sanitizing systems 20, as well as any of the sensors associated with the humidifier 10 and/or the user interface 92. Input/output ("I/O") signals may be routed between controller 90 and user interface/control panel 92 as well as other operational components of the humidifier 10. Controller 90 can execute and control the humidifier 10 in various humification and/or sanitizing operations or cycles.

Figure 4:
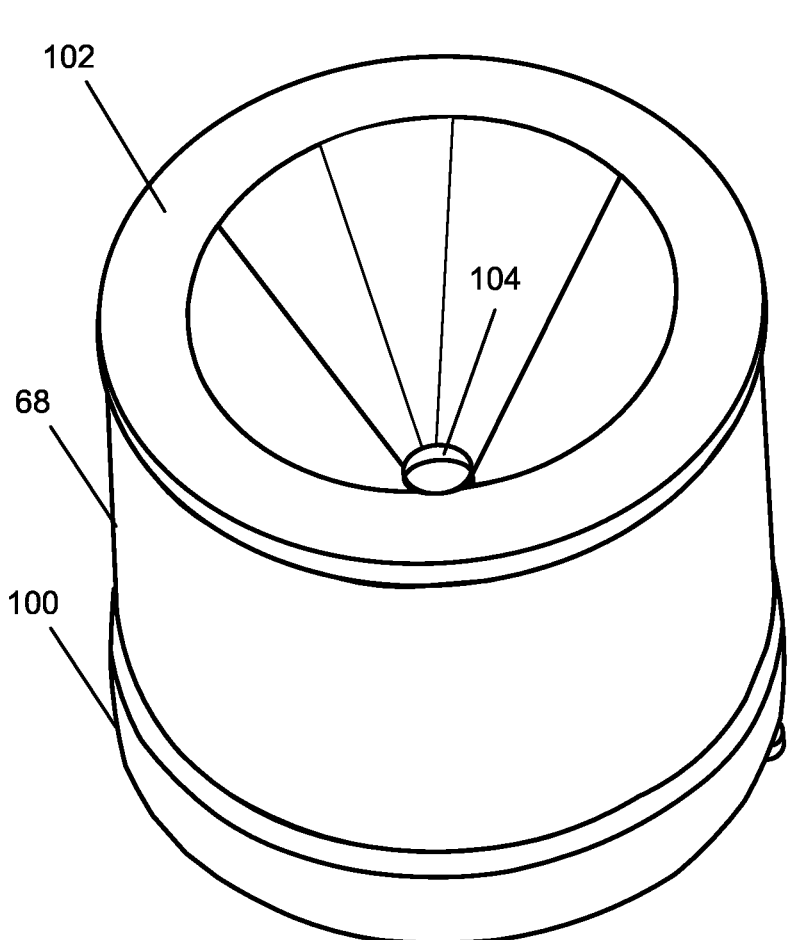
FIG. 4 is a top perspective view of one example of a wick assembly, consistent with the present disclosure.
Figure 5:
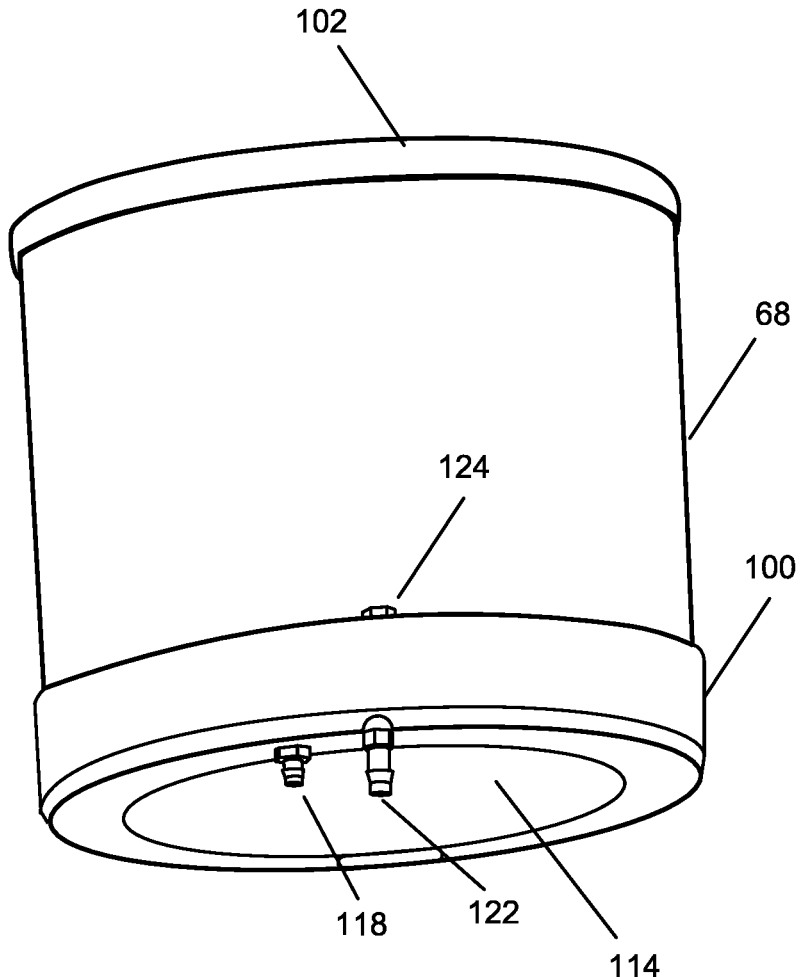
FIG. 5 is a bottom perspective view of the wick assembly of FIG. 4, consistent with the present disclosure.
Figure 6:
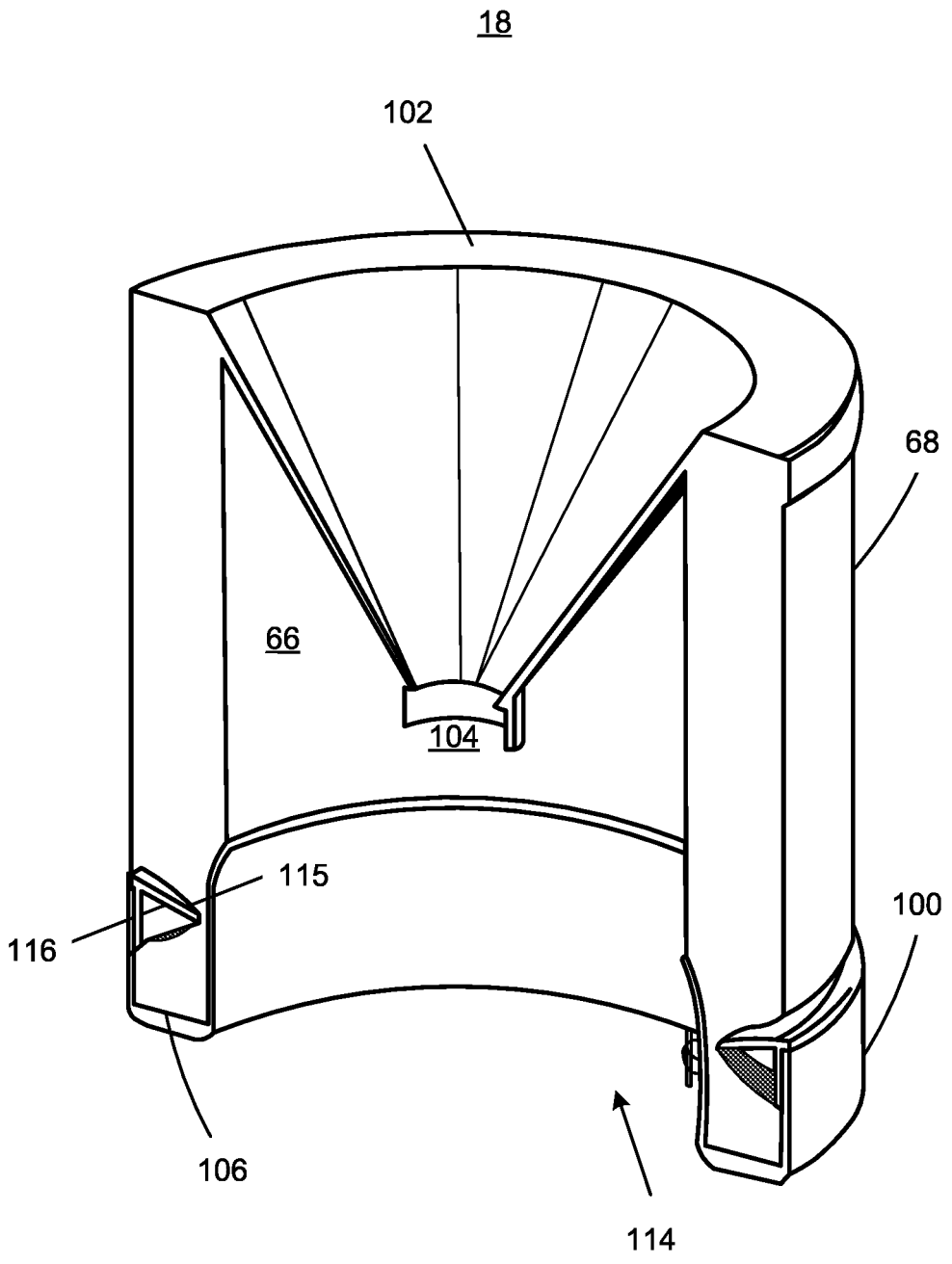
FIG. 6 is a cross-sectional perspective view of the wick assembly of FIG. 4, consistent with the present disclosure.
Figure 7:
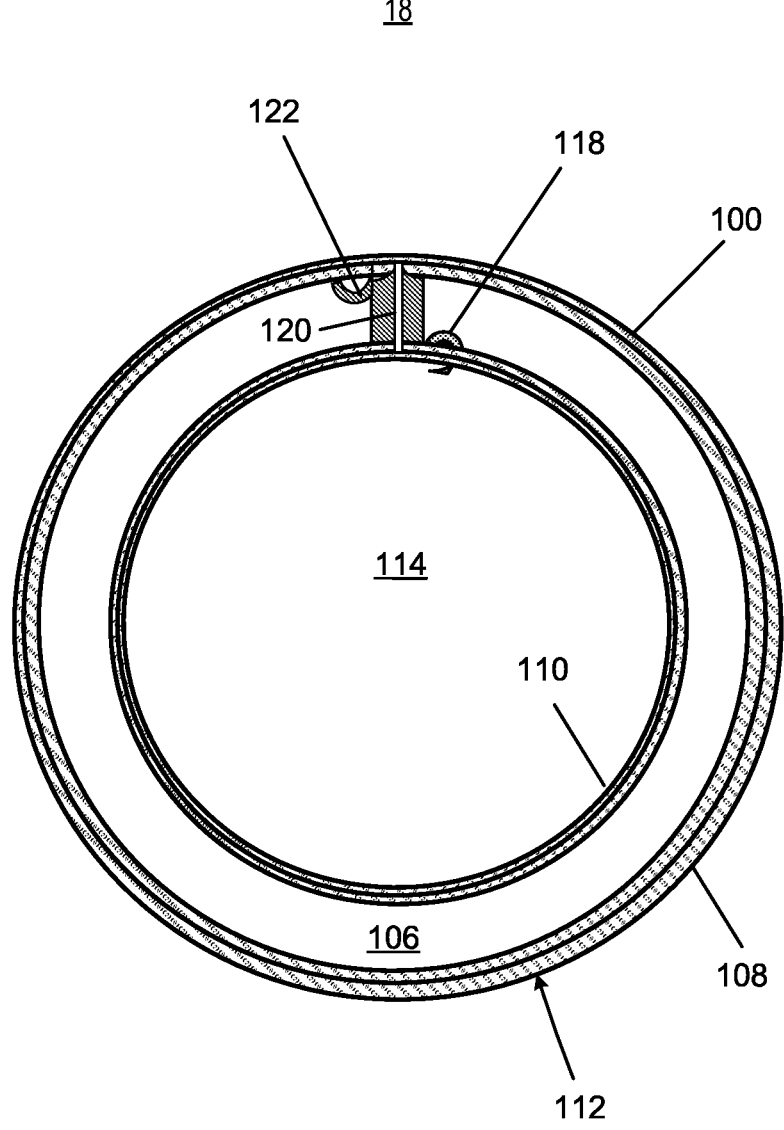
FIG. 7 is a cross-sectional top view of the wick cartridge of FIG. 4, consistent with the present disclosure.
Figure 8:
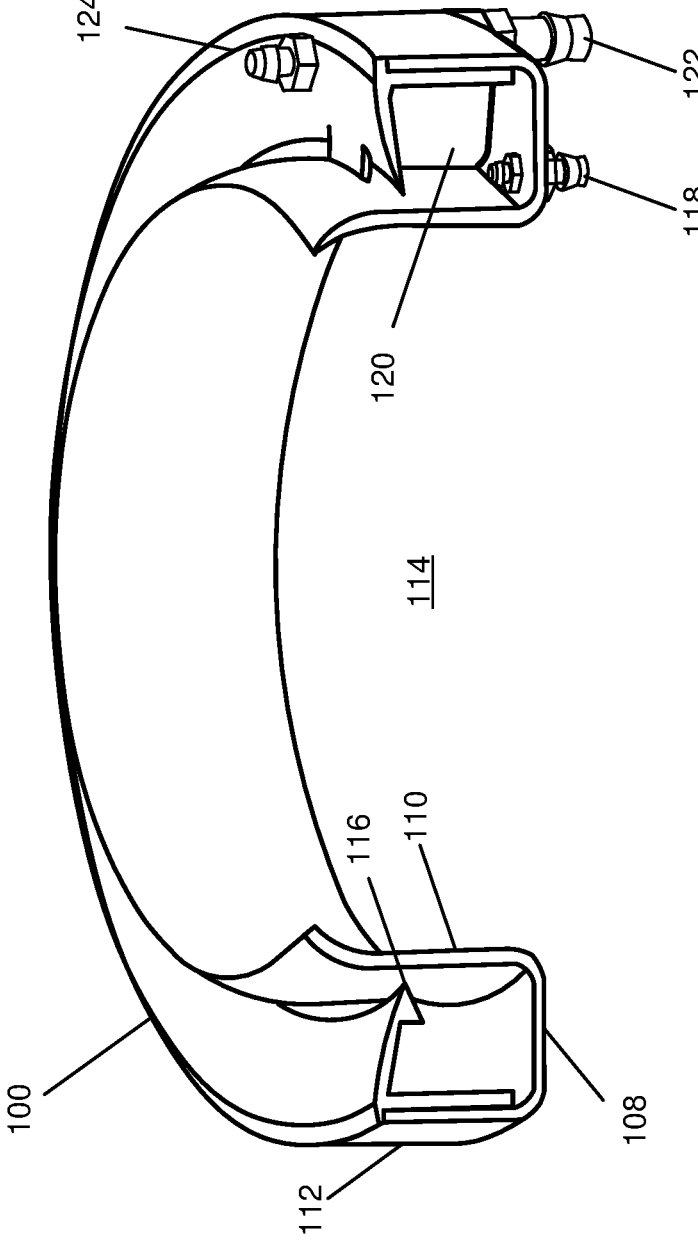
FIG. 8 is a further cross-sectional top view of the wick cartridge of FIG. 4, consistent with the present disclosure.
Figure 9:
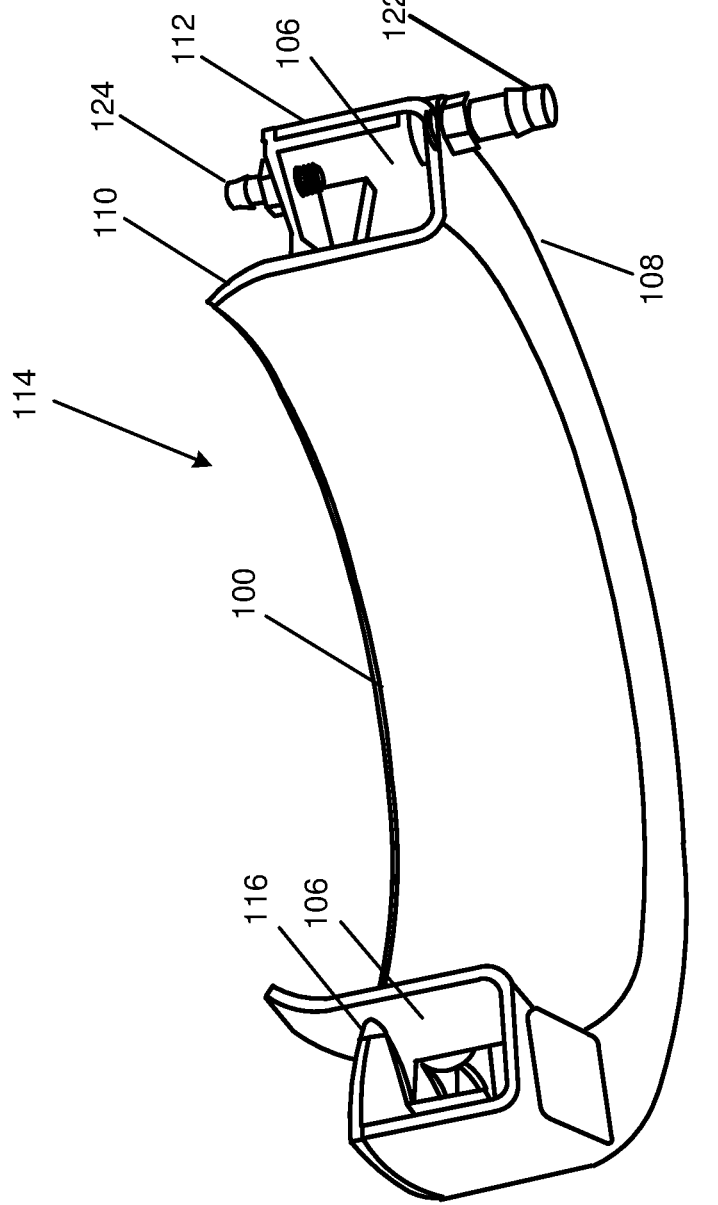
FIG. 9 is yet another cross-sectional top view of the wick cartridge of FIG. 4, consistent with the present disclosure.

Turning now to FIGS. 4-6, one example of the wick assembly 18 is generally illustrated.

The wick assembly 18 may include a wick 68 secured to a wick cartridge 100 and wick air cavity 66. Supply air 56 (which is either environmental or filtered environmental air) flows into the wick air cavity 66, and at least some of the supply air 56 flow through and/or past the wick 68, and water pumped by the water pump 48 from the water reservoir 14 is transferred (e.g., evaporated) from the wick 68 into the supply air 56 to create humidified air 70.

In the illustrated example, the wick assembly 18 includes a wick cover 102 that extends over a top of the wick 68. The wick cover 102 may include a passage 104 configured to allow the water inlet tube 32 may extend through the wick assembly 18. The wick cover 102 may also have a shape that generally corresponds to the shape of the funnel 28. As such, the wick air cavity 66 (best seen in FIG. 6) may be at least partially defined as a space/volume between the wick cartridge 100, the wick 68, and the wick cover 102. Alternatively, it should be appreciated that the wick cover 102 may be replaced by an extension of the wick 68. As such, the wick air cavity 66 may be at least partially defined as a space/volume between the wick cartridge 100 and the wick 68.

The wick 68 is configured to be secured to the wick cartridge 100 in any manner known to those skilled in the art. The wick 68 may include a material configured to absorb water in the wick assembly 18 (e.g., from the wick cartridge 100). For example, the wick 68 may include material configured to absorb water within the wick assembly 18 by way of capillary action. Non-limiting examples of materials that the wick 68 may include are sponges, foams (e.g., compressed cellulose foams), fibrous materials (e.g., webbed or pleated fibrous materials), clothes, and/or the like. In at least one example, the wick 68 may include a resiliently deformable material configured to be compressed within the wick cartridge 100. The compression of the wick 68 may secure the wick 68 to the wick cartridge 100 and/or generally prevent air from flowing between the wick 68 and the wick cartridge 100.

As noted above, the wick assembly 18 may optionally include a wick cover 102. The wick cover 102 may be secured (either permanently secured or removably secured) to the upper portion of the wick 68. In at least one example, the wick cover 102 may be sealed to the wick 68 to generally prevent air from flowing between the wick cover 102 and the wick 68. The wick cover 102 may include a passage 104 configured to allow the water inlet tube 32 may extend through the wick assembly 18. The passage 104 may be sealed to the water inlet tube 32 to generally prevent air from flowing between the wick cover 102 and the water inlet tube 32. The wick cover 102 may also have a shape that generally corresponds to the shape of the funnel 28. In some embodiments, the wick cover 102 may form the funnel 28. As such, the wick cover 102 may include a material that does not absorb water such as, but not limited to, plastic, rubber, or the like.

With reference to FIGS. 6-9, the wick cartridge 100 includes a water tray 106. The water tray 106 is configured to be in fluid communication with the water reservoir 14 and to hold a quantity of water. The wick cartridge 100 may be configured to receive at least a portion of the wick 68 such that the wick 68 is in contact with water disposed within the water tray 106 and capillary action causes the water to flow towards the opposite end of wick 68. The wick cartridge 100 may be permanently or removably secured to the wick 68. As may be appreciated, the water in the water reservoir 14 may include a sufficient amount of ozone to prevent and/or reduce the growth of bacteria, mold, and/or virus in the water reservoir 14. The water in the water tray 106 may also have a sufficient amount of ozone to prevent and/or reduce the growth of bacteria, mold, and/or virus in the wick assembly 18. Surprisingly, it has been found that the ozone in the water will sufficiently break down while passing through the wick 68 such that the humidified air 70 will have a biologically inert amount of ozone. As such, the humidifier 10 according to one example of the present disclosure does not need an ozone filter downstream of the wick assembly 18. It may be appreciated, however, that the humidifier 10 of the present disclosure may additionally include an ozone filter downstream of the wick assembly 18.

In at least one example, the wick cartridge 100 may have a generally annular configuration such that the water tray 106 extends generally circumferentially around the wick cartridge 100, though this is not a limitation of the present disclosure unless specifically claimed as such. The water tray 106 may include a base 108 and an inner sidewall 110 and outer sidewall 112 extending from the base 108. The supply air 56 may be configured to flow into the wick air cavity 66, for example, through one or more supply air wick cartridge inlet 114. The supply air wick cartridge inlet 114 may be configured to be in fluid communication with the housing 12 (e.g., the supply air inlet 64). The supply air wick cartridge inlet 114 may be at least partially defined by the base 108 and/or the inner sidewall 112 of the wick cartridge 100. The base 108 of the wick cartridge 100 may be configured to be sealed to the housing 12 (e.g., proximate the supply air inlet 64) to generally air from flowing between the wick cartridge 100 and the housing 12 and/or to generally direct all of the supply air 56 into the wick air cavity 66.

Figure 10:
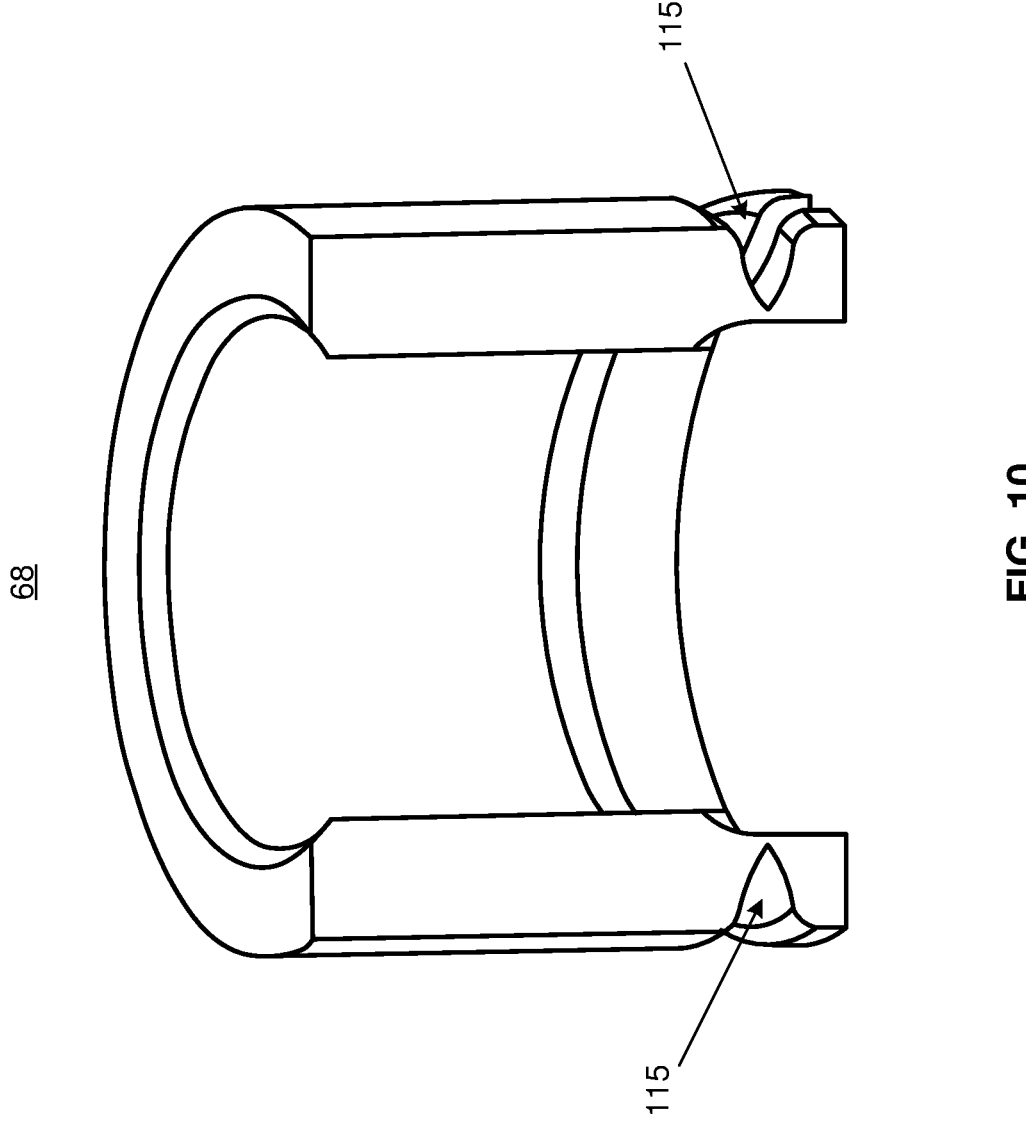
FIG. 10 is a cross-sectional view of one example of a wick, consistent with the present disclosure.

In at least one example, the wick cartridge 100 includes one or more wick retention protrusions 116. The wick retention protrusions 116 may extend from the inner or outer sidewalls 110, 112, and may be configured to secure the wick 68 to the wick cartridge 100, and to position the wick 68 such that it is at least partially disposed within the water tray 106. In the illustrated example, the wick retention protrusions 116 extend radially inward from the outer sidewall 112. A cross-section of the wick 68 showing the indentation 115 in the wick 68 caused by the wick retention protrusions 116 is generally illustrated in FIG. 10. As can be seen, the bottom of the wick 68 may have a generally annular and/or circular cross-section corresponding to the shape (e.g., annular and/or circular cross-section) of the water tray 106. Alternatively (or in addition), the wick retention protrusions 116 may extend radially outward from the inner sidewall 110. In either case, the wick retention protrusions 116 may extend continuously from the inner or outer sidewall 110, 112 and/or along one or more portions of the inner or outer sidewall 110, 112. The wick retention protrusions 116 may be configured to create a pinch point that generates a compressive force against the wick 68. This compressive force not only secures the wick 68 to the wick cartridge 100, but also generally prevents air from flowing between the wick cartridge 100 and the wick 68. The air seal between the wick cartridge 100 and the wick 68 may allow for a slight pressurization of the water in the water tray 106, thereby enhancing the capillary effect.

As described herein, water may be pumped by the water pump 48 from the water reservoir 14 to the wick cartridge 100, for example, to the water tray 106. The wick cartridge 100 may include at least one water inlet port 118 (best seen in FIGS. 5 and 8) configured to fluidly couple the water tray 106 to the water reservoir 14. In particular, the water pump 48 may draw water from the water reservoir 14 through tubing or the like to the water inlet port 118. The water may flow into the water tray 106 to at least partially fill up the water tray 106 with water such that the wick 68 is at least partially submerged in the water in the water tray 106.

The water tray 106 may optionally include a divider wall 120. The divider wall 120 extends from the base 108 between the inner and outer sidewalls 110, 112. The water inlet port 118 may be disposed proximate to one side of divider wall 120, and one or more optional water outlet ports 122 may be disposed on the opposite side of the divider wall 120. As a result, water pumped to the water tray 106 may enter the water tray 106 proximate one side of the divider wall 120 through the water inlet port 118, flow around the water tray 106 to the opposite side of the divider wall 120, and drain out of the water tray 106 through the water outlet ports 122, e.g., back to the water reservoir 14. This configuration allows the water pump 46 to operate generally at one or more fixed values, and any excess water (i.e., water pumped into the water tray 106 by the water pump 46 in excess of the amount of water that is transferred to the supply air 56) can be returned to the water reservoir 14 to avoid over-filling the water tray 106. This design also greatly simplifies the necessary controls of the water pump 46. The opening to the water outlet ports 122 within the water tray 106 may be optionally disposed at a desired water level (e.g., height) within the water tray 106. As such, the position (e.g., height) of the opening to the water outlet ports 122 may be selected depending upon how much the wick 68 is to be submerged in the water with the water tray 106.

The wick cartridge 100 may include at least one air bleed port 124. The air bleed port 124 may be configured to allow air within the water tray 106 to be removed from the water tray 106 as water is pumped into the water tray 106. The opening to the water outlet ports 122 may be selected such that the air bleed port 124 is partially submerged in the water within the water tray 106, but water does not flow out of the air bleed port 124.

Figure 12:
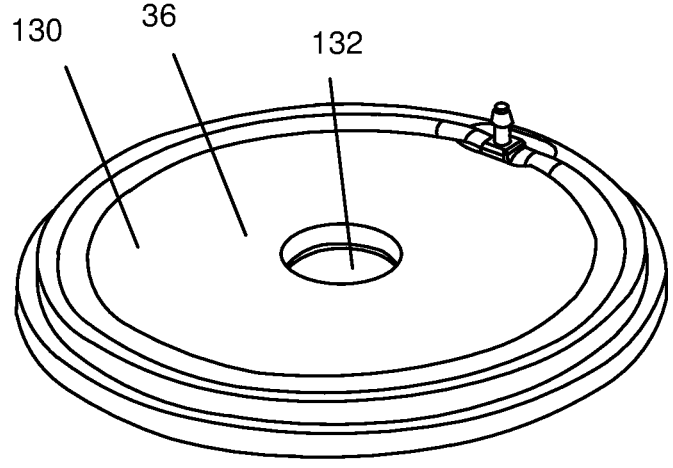
FIG. 12 is a top perspective view of one example of an ozone distribution system, consistent with the present disclosure.
Figure 13:
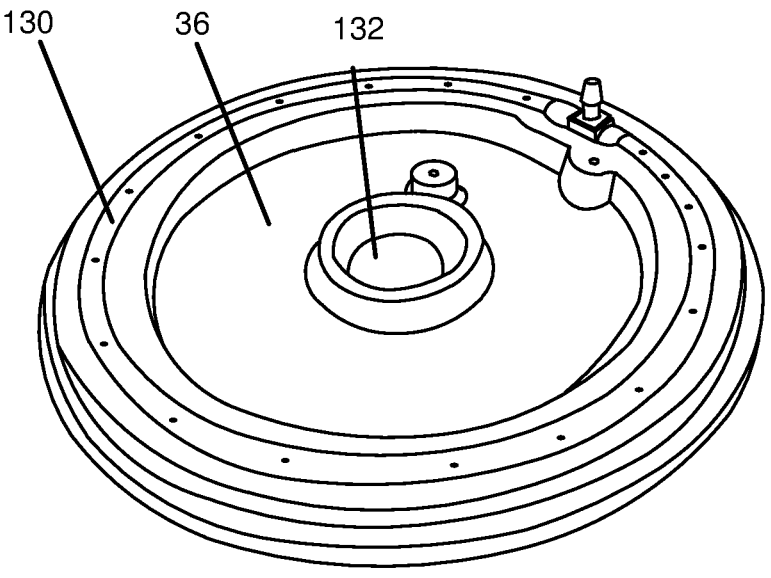
FIG. 13 is a top perspective view of another example of an ozone distribution system, consistent with the present disclosure.

Turning now to FIGS. 12 and 13, examples of an ozone distribution system 130 are generally illustrated. The ozone distribution system 130 may be fluidly coupled to the ozone generator 74 and the air pump 76 and is configured to cause the ozone gas to be dispensed/distributed directly into the water within the water reservoir 14 (e.g., in the form of ozone bubbles). As noted herein, the ozone bubbles may be selected such that a sufficient amount of ozone is absorbed into the water within the water reservoir 14. The ozone distribution system 130 may therefore be located at the bottom or base 36 of the water reservoir 14. In at least one example, the ozone distribution system 130 may include one or more rings with a plurality of ozone openings configured to allow ozone to bubble out into the water. The number and size of the ozone openings will depend on the desired flow rate of ozone. In at least one example, the ozone distribution system 130 may include one or more rings of perforated tubing.

The bottom or base 36 of the water reservoir 14 may optionally include a water inlet cavity 132. The water inlet cavity 132 may be configured to receive the distal or bottom end of the water inlet tube 32. In particular, the water inlet cavity 132 may be configured such that a sufficient amount of water remains in the water reservoir to ensure that the outlet 34 of the water inlet tube 32 remains submerged, even in the event that the water level 44 of the water reservoir is empty. This generally prevents gas (e.g., ozone) in the headspace 76 from being able to escape up the water inlet tube 32 when the water in the water reservoir 14 is empty. In the example of FIG. 12, the water inlet cavity 132 is formed as a recessed region in the bottom or base 46 of the water reservoir 14. Alternatively (or in addition), the water inlet cavity 132 may be formed by one or more sidewalls extending upwardly from the bottom or base 46 of the water reservoir 14. In either example, the water pump 46 may draw water from the water reservoir from an area outside of the water inlet cavity 132.

As used herein the term "about," when used in connection with a value or a range, means plus or minus 5% of the indicated value or the endpoints of the range. Thus, for example, about 5% means 4.75% to 5.25%. Similarly, about 5 to about 10% means 4.75 to 10.5.

From time to time the present application describes features using numerical ranges. Such ranges should be understood to include the recited endpoints, and to encompass any intermediate ranges within the stated range. Thus, for example, the range "1 to 10" should be understood to include the endpoints 1 and 10, as well intermediate ranges therein (e.g., from 1 to 9, 2 to 10, 2 to 9, 3 to 9, 4 to 9, etc.) as if those intermediate ranges were expressly recited.

Figure 14:
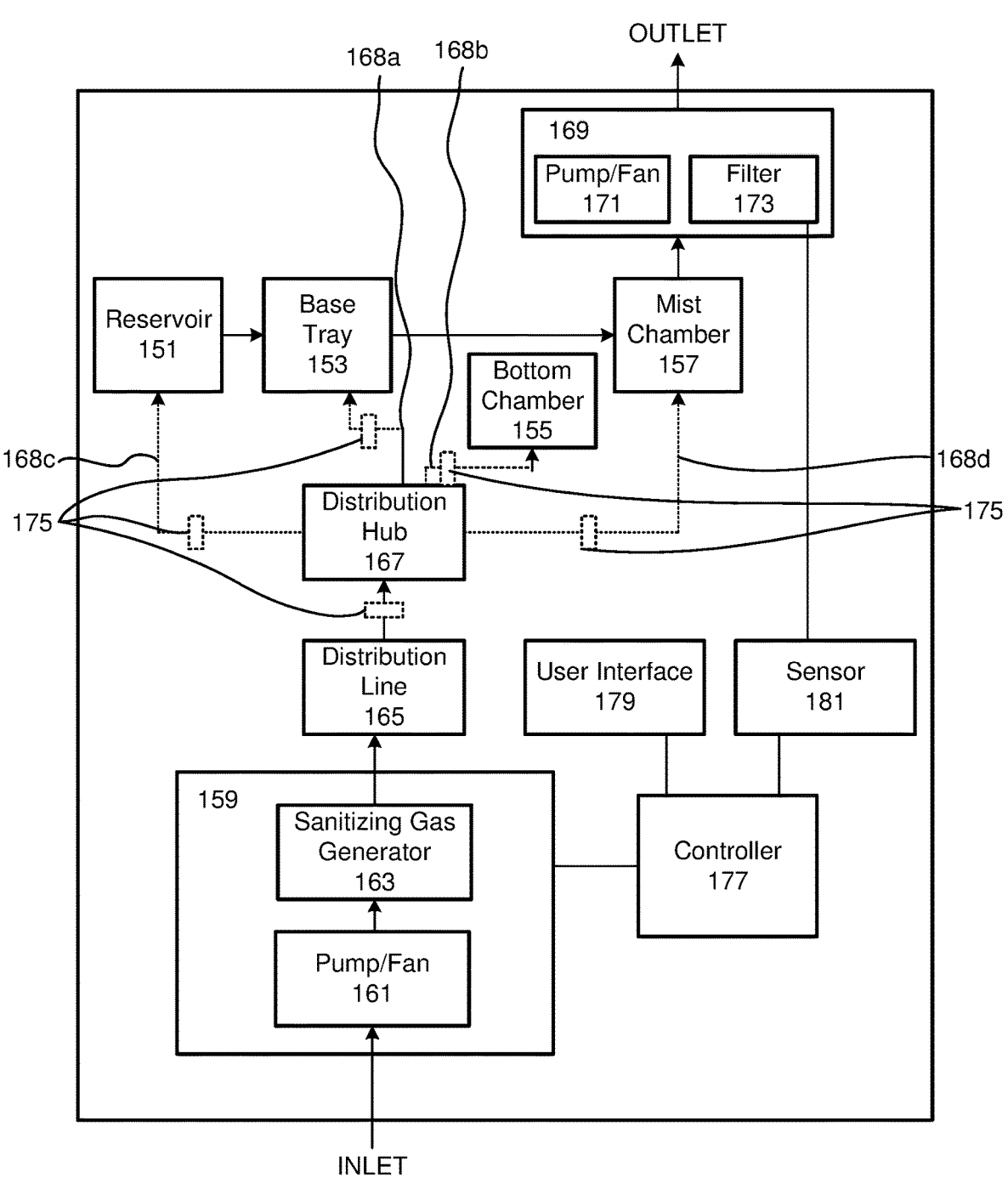
FIG. 14 is block diagram of one example of a self-sanitizing humidifier consistent with the present disclosure.

FIG. 14 is a block diagram of one example of a self-sanitizing humidifier consistent with the present disclosure. As shown, humidifier 150 includes a reservoir 151, base tray 153, bottom chamber 155, and a mist channel 157. During a normal humidification operation (e.g., to produced humidified air), liquid (e.g., water) within reservoir 151 is conveyed into base tray 153, and is converted to air born droplets (mist) in any suitable manner. For example, a nebulizer (e.g., a membrane vibrating at ultrasonic or another suitable frequency) may convert liquid within base tray 153 into air born droplets proximate the bottom of the mist channel of the humidifier. The droplets may be conveyed through the mist channel and into the surrounding environment with a flow of air generated by an air pump and/or fan disposed in the bottom chamber of the humidifier, which is fluidly coupled with the mist channel.

According to another aspect humidifier 150 further includes a sanitizing gas supply system 159, which is generally configured to supply a sanitizing gas (e.g., ozone) for use in a sanitizing operation. In the embodiment of FIG. 14, the sanitizing gas supply system 159 includes an air pump/fan 161 and a sanitizing gas generator 163. In embodiments, the air pump/fan 161 is configured to supply inlet air from an inlet to the sanitizing gas generator 163, and the sanitizing gas generator 163 is configured to generate a sanitizing gas at least in part from the inlet air. For example, sanitizing gas generator 163 may be an ozone generator that is configured to generate ozone gas at least in part from inlet air provided by pump/fan 161. Any suitable ozone generator may be used for that purpose, provided it can generate ozone at least in part from inlet air. Without limitation, in embodiments sanitizing gas generator 163 is an ozone generator that is sized and configured to fit within the body of humidifier 150. In other words, in some embodiments sanitizing gas generator 163 (and/or sanitizing gas supply system 159) is integral with a body of humidifier 150.

As shown in FIG. 14, humidifier 150 further includes a distribution line 165 that is fluidly coupled to sanitizing gas generator 163, and which is fluidly coupled to one or more components of humidifier 150. For example, a distal end of distribution line 165 may be fluidly (and in some instances, directly) coupled to reservoir 151, base tray 153, bottom chamber 155, mist channel 157, or a combination of two or more thereof. Alternatively and as shown in FIG. 14, humidifier 150 may optionally include a distribution hub 167 that is fluidly coupled to a distal end of distribution line 165.

In general, distribution hub 167 is configured to distribute a flow of sanitizing gas (e.g., ozone) from distribution line 165 to one or more components of humidifier 150. In that regard, distribution hub 165 may include or be fluidly coupled to one or more channels 168a-168d, which in turn are fluidly coupled to one or more components of humidifier 150. For example, distribution hub 165 may include or be fluidly coupled to a first channel 168a, which is fluidly coupled to reservoir 153. The distribution hub 165 may further include or be fluidly coupled to a second distribution channel 168b, which is fluidly coupled to bottom chamber 155. The distribution hub 165 may also include or be fluidly coupled to a third distribution channel 168c, which is fluidly coupled to reservoir 151. And still further, distribution hub 165 may include or be fluidly coupled to a fourth distribution channel, which is fluidly coupled to mist channel 157. A check valve 175 may be coupled to each distribution channel 168a-168d. When used, such check valves may function to prevent the back flow of liquid into distribution hub 167 from respective components of humidifier 150.

In embodiments, distribution hub 167 is preconfigured to supply a pre-determined flow of sanitizing gas to each of the distribution channels to which it is fluidly coupled. Alternatively, distribution hub 167 may include one or more valves, which may be electronically controlled (e.g., by a control system 177) to adjust a flow of sanitizing gas to each channel to which the distribution hub 167 is fluidly coupled and, thus, to the components of humidifier 150 that are attached to each respective distribution channel.

FIG. 14 depicts an example of a humidifier consistent with the present disclosure, and which includes a single sanitizing gas supply system, a single distribution line, a single distribution hub, and distribution channel(s) that are coupled to a single element of the humidifier. The embodiment of FIG. 14 is for the sake of example only, and the technologies of the present disclosure are not limited to the illustrated configuration. Indeed, the technologies of the present disclosure may use any suitable number of sanitizing gas supply systems in combination with any suitable number of distribution lines, distribution hubs, and distribution channels. Moreover, a single distribution line may be fluidly coupled to multiple sanitizing gas generators, multiple distribution hubs, and/or multiple components of a humidifier. Likewise, multiple distribution channels may be fluidly coupled to a single component of a humidifier, and/or a single distribution line may be fluidly coupled to multiple components of a humidifier. Moreover, the technologies described herein may be used with any type of humidifier.

Humidifier 150 further includes an exhaust system 169. In general, exhaust system 169 functions to prevent or substantially prevent the flow of sanitizing gas into the atmosphere surrounding humidifier 150. In embodiments, exhaust system 169 includes an optional pump/fan 171 and a filter 173. When used, pump/fan 171 may be configured to facilitate the flow of sanitizing gas towards and/or through filter 173. Without limitation, in some embodiments pump/fan 161 and pump/fan 171 are configured in a so-called "push/pull" configuration, in which pump/fan 161 pushes air and sanitizing gas through humidifier 150, and pump/fan 171 pulls air and sanitizing gas through humidifier 150 towards and through filter 173.

Filter 173 is generally configured to absorb the sanitizing gas and/or to convert the sanitizing gas to another composition (e.g., a breathable gas) that is safe for discharge into the environment. Non-limiting examples of suitable filters that may be used for such a purpose include magnesium oxide filters and activated carbon filters. In embodiments, filter 173 is or includes magnesium oxide, and is configured to convert sanitizing gas (e.g., ozone) to a breathable gas (e.g. oxygen).

Humidifier 150 may further include a controller 177 and a user interface 179. In general, controller 177 functions to control the operation of various components of humidifier 150, including but not limited to sanitizing gas generator 163 and nebulizer/or fan (both not shown) responsible for generating humidified air (e.g., for generating moisture droplets and/or for conveying a flow of air over a wick). Put differently, controller 177 may function to control the performance of humidification operations and sanitization operations by humidifier 150. As used herein, "humidification operations" refer to operations performed by humidifier 150 in connection with the generation of humidified air. Non-limiting examples of such operations may include the [production of liquid droplets (e.g., by a nebulizer), operation of one or more humidification fans (e.g. to form humidified air via an airflow over a wick), etc. In contrast, the term "sanitization operations" generally refers to operations performed by humidifier 150 in connection with the sanitization of one or more components thereof. Non-limiting examples of sanitization operations include operation of pump/fan 161, operation of sanitizing gas generator 163, operation of pump/fan 171, filter detection operations (discussed below), combinations thereof, and the like.

User interface 179 is generally configured to enable a user to initiate the performance of humidification operations and/or sanitization operations by humidifier 179. In embodiments, user interface 179 may include one or more control surfaces, buttons, switches, combinations thereof, and the like, which enable a user to initiate and/or cancel the performance of a humidification operation or a sanitization operation. In those or other embodiments, controller 177 may be programmable, e.g., via user interface 179 or in another manner (e.g., a wired or wireless communication interface), to enable a user to schedule the performance of humidification and/or sanitization operations by humidifier 150. In such instances, controller 177 and/or user interface 179 may include a timer that monitors the length of performance of a humidification and/or sanitization operation. When such a timer is used, user interface 179 may include a display for indicating a remaining time for a sanitization and/or humidification operation to a user. Of course the display is not limited only to indicating the remaining time for such operations, and may be utilized to indicate any suitable information to a user.

In embodiments and as shown in FIG. 14, humidifier may optionally include one or more sensors 181. In general, sensors 181 are configured to monitor characteristics of humidifier 150 to ensure safe performance of a sanitization operation. For example, in embodiments filter 173 is configured to move between an installed and uninstalled position (in the case of a removable filter), and/or between an open and a closed position (in the case of a retractable filter). In such instances, operation of sanitizing gas generator 163 while the filter is not installed or is in an open position may cause sanitizing gas to be emitted into the surrounding environment, e.g., via mist channel 157. This may be undesirable in instances where the sanitizing gas has a negative or unknown impact on human health.

With that in mind, sensors 181 may include a filter detection sensor that is configured to monitor the position of filter 173 and to output a filter detection signal to controller 177. Any suitable filter detection sensor may be used. For example, a filter detection sensor in the form of or including an optical sensor for detection a position of the filter may be used. Alternatively or additionally, the filter detection sensor may include or be in the form of a latch, button, switch, or the like, which is pressed, depressed, or the like when the filter is in the closed position, and is released (i.e., not pressed or depressed) when the filter is in the open position. Still further, the filter detection sensor may include a conductive pad that is configured to electrical couple with a corresponding conductive pad on the filter when the filter is in the closed position—resulting in a detectable change in electrical properties, e.g., conductivity, resistance, voltage, etc. that can be conveyed in a filter detection signal.

The filter detection signal is indicative of the position of filter 173, and controller 177 can determine a position of filter 173 based at least in part on the filter detection signal. When it is determined that filter 173 is not installed or is in the open position, controller 177 may prevent or disable operation of one or more components of humidifier 150 sanitizing gas generator 163, fan/pump 161, and/or fan/pump 171. Without limitation, in embodiments controller 173 prevents or disables operation of sanitizing gas generator 163 when filter 173 is not installed or is in an open position.

Sensors 181 may also include one or more sanitizing gas sensors. When used, the sanitizing gas sensors may be configured to sense the presence and/or concentration of sanitizing gas within one or more components of humidifier 150. In that regard, sanitizing gas sensors may be used to detect the presence and/or concentration of sanitizing gas within reservoir 151, base tray 153, bottom chamber 155, mist channel 157, distribution line 165, distribution hub 167, and/or distribution channels 168a-168d. Without limitation, in some embodiments sensors 181 include sanitizing gas sensors that are configured to sense the presence and/or concentration of sanitizing gas within at least bottom tray 153 and/or reservoir 151. The sanitizing gas sensors may function to sense the presence of sanitizing gas and to output a gas sensor signal to controller 177, wherein the gas sensor signal is indicative of the presence and/or concentration of the sanitizing gas in one a respective component of humidifier 150. In such instances controller 177 may determine the presence and/or concentration of sanitizing gas within humidifier 150 based at least in part on the gas sensor signal. In embodiments, controller 177 is configured to prevent and/or disable performance of a humidification operation when it is determined that sanitizing gas is present within humidifier 150. Alternatively, controller 177 may determine a concentration of sanitizing gas within humidifier 150 (or a component thereof) and compare the determined concentration to a threshold concentration of sanitizing gas. When the determined concentration is greater than or equal to the threshold concentration, controller 177 may disable or prevent performance of a humidification operation. When the determined concentration is below the threshold concentration, however, controller 177 may permit the performance of a humidification operation.

Figure 15A:
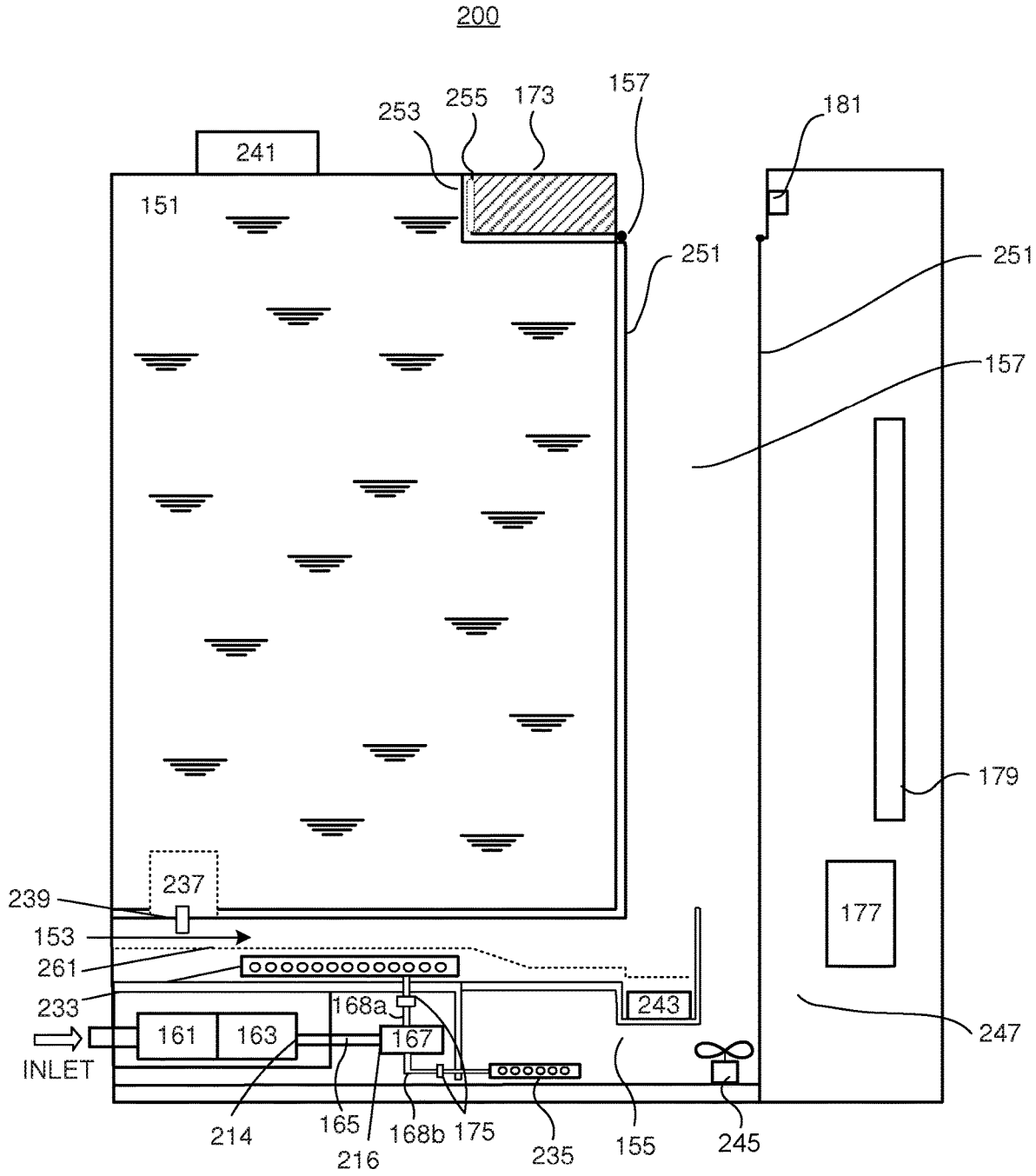
FIG. 15A is cross sectional diagram of one example of a self-sanitizing mist humidifier consistent with the present disclosure, with a filter in an open position.
Figure 15B:
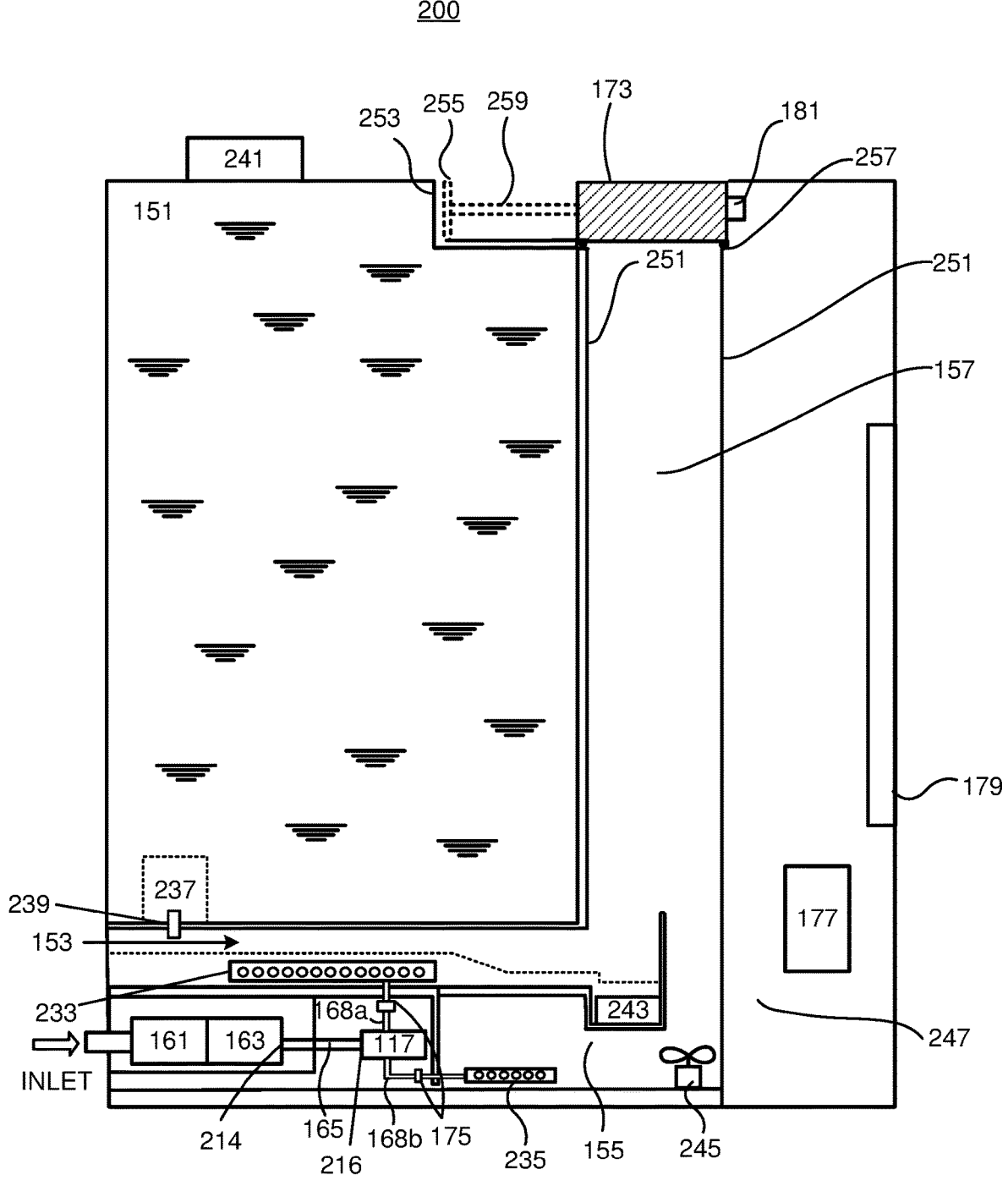
FIG. 15B is cross sectional diagram of the self-sanitizing mist humidifier of FIG. 15A, with the filter in a closed position.

FIG. 15A depicts one example of a mist humidifier 200 consistent with the present disclosure, wherein the mist humidifier 200 includes retractable filter 173 in an open position. FIG. 15B depicts the same mist humidifier with retractable filter 173 in a closed position. As shown, mist humidifier 200 includes a reservoir 151, base tray 153, bottom chamber 155, and mist channel 157, inlet fan/pump 161, sanitizing gas generator 163, distribution line 165, distribution hub 167, filter 173, controller 177, user interface 179, and filter sensor 181. The nature and function of such components is generally the same as described above in connection with FIG. 14, and so is not reiterated in detail the interest of brevity.

Reservoir 151 optionally includes a demineralization cartridge 237, and includes an outlet 239 and an inlet 241. The inlet 241 may include a filter (e.g., a lid for enclosing the inlet 241 may include a filter therein). When used, the demineralization cartridge 237 functions to remove minerals from liquid (e.g., water) within reservoir 151. A wide range of demineralization cartridges are known in the art, and any suitable demineralization cartridge may be used.

The reservoir 151 includes two opposing sidewalls, a top, and a bottom (all not labeled). As shown in the embodiment of FIGS. 15A and 15B, inlet 241 is disposed on the top of reservoir 151, and outlet 239 is disposed on the bottom of reservoir 241. Inlet 241 may be configured in any suitable manner that enables a user to fill of reservoir 151 with a liquid. Without limitation, in embodiments inlet 241 includes a threaded opening within the top of reservoir 151, and a corresponding threaded cap. Alternatively, inlet 241 includes an opening through the top of reservoir 151, and a plug for sealing the opening. Notably, users may find it easier to fill reservoir 151 due to the placement of inlet 241 on the top thereof.

Various types of reservoir outlets for humidifiers are known, and any suitable outlet may be used for outlet 239. In embodiments, reservoir 151 is removable from humidifier 200. In such instances, outlet 239 is or includes a valve that is biased (e.g., by a spring) in a closed position when reservoir 151 is removed from humidifier 151. When reservoir 151 is reinstalled in the humidifier 200, the bias force applied by the spring may be overcome (e.g., by interaction of the base and a component of outlet), moving the valve from a closed to an open position and allowing liquid (e.g., water) to flow from reservoir 151 into base tray 153. Alternatively, reservoir 151 may be permanently (i.e., non-detachably) coupled to body 253 of humidifier 200. In such instances, outlet 239 may simply be in the form of an opening. Still further, outlet 239 may include or be in the form of an electronically actuatable valve that is controllable, e.g., by controller 177.

The embodiment of FIGS. 15A and 15B further includes first and second distribution channels 168a, 168b, which are respectively coupled to distribution hub 167 and to first and second diffusers 233, 235. A check valve 175 is disposed on each of the first and second distribution channels 168a, 168b, and functions in the same manner as described above in connection with FIG. 14. The first diffuser 233 is disposed within the base tray 153 and is configured to distribute sanitizing gas within the base tray 153 during a sanitization operation. Similarly, the second diffuser 235 is disposed within the bottom chamber 155 and is configured to distribute sanitizing gas within the bottom chamber 155 during a sanitizing operation. In embodiments, first diffuser 233 is disposed beneath a liquid level 261 within base tray 153—facilitating the distribution of sanitizing gas into the liquid by first diffuser 233.

Additionally, or alternatively, in some instances, a diffuser may be disposed within the reservoir 151. For example, a flexible distribution channel may couple the diffuser to the sanitizing gas generator 163 such that the diffuser can be removably disposed within the reservoir 151.

Humidifier 200 further includes a nebulizer 243 and a mist fan 245. Nebulizer 243 is generally configured to convert liquid within base tray 153 into mist, i.e., air born droplets. A wide variety of nebulizers are known in the art for use in humidifiers, and any suitable nebulizer may be used as nebulizer 243. In embodiments nebulizer 234 is in the form of or includes a membrane that is configured to vibrate at a frequency suitable for converting liquid into mist, e.g., ultrasonic or other suitable frequency. The membrane may be made of any suitable material, such as metal (e.g., titanium, aluminum, etc.), a metal alloy, a polymer, combinations thereof, and the like. Without limitation, in embodiments nebulizer 243 is a metal (e.g., titanium) membrane that is configured to vibrate at an ultrasonic frequency to produce mist, e.g., proximate a bottom of mist channel 157

Mist fan 245 generally functions to facilitate the conveyance of mist formed by nebulizer 243 through mist channel 157. For example, mist fan 245 may function to produce an airflow that is directed towards an opening in mist channel 157. The airflow produced by mist fan 245 combines with the mist generated by nebulizer 243 to form humidified air, which migrates through mist channel 157 and into the environment surrounding humidifier 200.

In the embodiment of FIGS. 15A and 15B, mist fan 245 is disposed within bottom chamber 155, wherein bottom chamber 155 is in fluid communication with mist channel 157. This illustration is for the sake of example only, and mist fan 245 may be positioned at any suitable location to facilitate the production of humidified air and the flow of humidified air through a mist channel and into a surrounding environment.

As noted above, humidifier 200 further includes filter 173. In this embodiment filter 173 is a retractable filter that is configured to move from an open position (shown in FIG. 15A) to a closed position (shown in FIG. 15B). Filter 173 may be moved between the open and the closed position in any suitable manner. For example, filter 173 may be manually moved between the open and the closed position. Alternatively or additionally, the position of filter 173 may be controlled electronically, e.g., by controller 177. In the latter instance, humidifier 173 may include an actuator 255 or other movement means that is configured to move filter 173 between an open and closed position, e.g., in response to a control signal from controller 177. For example and as shown in FIGS. 15A and 15B, actuator 255 may include an actuator arm 259 that is coupled to filter 173, e.g., to a side thereof. When used, actuator arm 259 may extend or retract in response to a control signal from controller 177, to move filter from an open position (FIG. 15A) to a closed position (FIG. 15B).

In the closed position, filter 173 may generally cover and/or seal mist channel 157. In embodiments, in the closed position filter 173 covers mist channel 157 and forms a seal (e.g., a gas tight seal) with body 247 of humidifier 200. In that way, filter 173 may hinder or even prevent escape of sanitizing gas into the surrounding environment during a sanitization operation. Put differently, due to the seal formed by filter 173, all or a portion of the sanitizing gas introduced into humidifier 200 during a sanitization operation will flow into filter 173. As filter 173 is configured to absorb or convert the sanitizing gas (e.g., into oxygen), filter 173 can effectively limit or prevent the emission of sanitizing gas into the surrounding environment.

Humidifier 200 may further include one or more sealing elements 257. In general, sealing element(s) 257 facilitate formation of a seal between filter 173 and body 247. Any suitable type and configuration of sealing element may be used for that purpose. In embodiments, sealing element 257 is in the form of a rubber sealing element, such as a rubber or gasket that extends around the perimeter of mist channel 157. The sealing element may be disposed on a shoulder proximate an opening of mist channel 157, as shown in FIGS. and 15B. Alternatively, mist channel 157 and/or body 247 may include one or more channels, and sealing element 257 may be disposed in such channels such that it can form a seal with filter 173 when filter 173 is in a closed position.

In the illustrated embodiment, humidifier 200 further include filter sensor 181. In general, filter sensor 181 functions to sense a position of filter 173. As discussed above in connection with FIG. 14, filter sensor 181 may provide a filter sensor signal to controller 177, and controller 177 may determine a position of the filter 173 based at least in part on the filter sensor signal. Depending on the position of the filter 173, controller 177 may permit or prevent performance of a sanitization operation.

Humidifier 200 may further include a user interface 179, which is configured to enable a user to initiate a humidification or sanitization operation by humidifier 200. During a humidification operation, liquid (e.g., water) within base tray 153 is converted to mist by nebulizer 243. The mist is conveyed through mist channel 157 by an airflow generated by mist fan 245.

In embodiments, in response to initiation of a sanitization operation via user interface 179, controller 177 determines a position of filter 173 based at least in part on a filter sensor signal provided by sensor 181. When filter 173 is in the open position (as shown in FIG. 15A), controller 177 may prevent the sanitization operation from being performed. When filter 173 is in the closed position (shown in FIG. 15B), however, controller 177 may permit performance of the sanitization operation. In such instances, controller 177 may cause inlet fan/pump 161 and/or sanitizing gas generator 163 to be energized. Inlet fan/pump may provide inlet air to sanitizing gas generator 163. Sanitizing gas generator 163 may utilize the inlet air to generate a sanitizing gas (e.g., ozone). The sanitizing gas may flow from sanitizing gas generator 163 into distribution line 165 and into distribution hub 167. From the distribution hub, the sanitizing gas may flow into first and second distribution channels 168a and 168b.

Sanitizing gas within the first sanitizing channel 168a flows into first diffuser 233 and into base tray 153—whereupon it will sanitize surfaces of base tray 153, as well as any liquid and/or air within base tray 153. Sanitizing gas within second distribution channel 168b flows into second diffuser 235, and into bottom chamber 155—whereupon it wills sanitize surfaces of bottom chamber 155, as well as any liquid and/or air within bottom chamber 155. At least a portion of residual sanitizing gas within base tray 153 and/or bottom chamber 155 will migrate (e.g., flow) into mist channel 157. During that time, sanitizing gas may be brought into contact/proximity with nebulizer 243—whereupon it may sanitize nebulizer 243, any air/liquid (if any) proximate nebulizer 243. Flow of sanitizing gas through mist channel 157 may be facilitated by an airflow generated by mist fan 245. As sanitizing gas flows through mist channel 157, it will sanitize sidewalls 251 thereof. At least a portion of the sanitizing gas within mist channel 157 will flow into filter 173—whereupon it will be absorbed by filter 173 and/or converted by filter 173 into a breathable gas. For example, in embodiments where filter 173 is a magnesium oxide filter and the sanitizing gas is ozone, filter 173 will function to convert ozone into oxygen. The breathable gas may then be exhausted into the environment.

Although not shown in FIGS. 15A and 15B, humidifier 200 may further include one or more sanitizing gas sensors. When used, such sensors may function to detect the presence and/or concentration of sanitizing gas within one or more components of humidifier 200. For example, sanitizing gas sensors may be placed and configured to detect the presence and/or concentration of sanitizing gas within base tray 153, bottom chamber 155, mist channel 157, and the like. When used, the sanitizing gas sensors may provide a gas sensor signal to controller 177, wherein the gas sensor signal is indicative of the presence and/or concentration of sanitizing gas within humidifier 177. In such instances, controller 177 may determine the presence and/or concentration of sanitizing gas within humidifier 200 based on the gas sensor signal.

In embodiments, controller 177 may determine a concentration of sanitizing gas within humidifier 200, and compare the determined concentration to a threshold concentration. When the determined concentration is greater than or equal to the threshold concentration, controller 177 may execute one or more safety operations to prevent unintended exhaust of sanitizing gas into the environment. For example, controller 177 may cause a warning indicator to appear on user interface 179, alerting a user to the presence of sanitizing gas within humidifier 200 and that filter 173 should not be advanced to the open position. Alternatively or additionally, when the position of filter 173 is controlled by controller 177, controller 177 may lock filter 173 in the closed position until the concentration of sanitizing gas falls below a threshold level.

In some embodiments the threshold concentration may be 0—meaning that controller 177 may execute one or more safety operations when sanitizing gas is detected within humidifier 200. In other embodiments threshold concentration is greater than 0, and controller 177 may execute one or more safety operations when it determines that a detected concentration of sanitizing gas is greater than or equal to the threshold concentration.

Figure 16A:
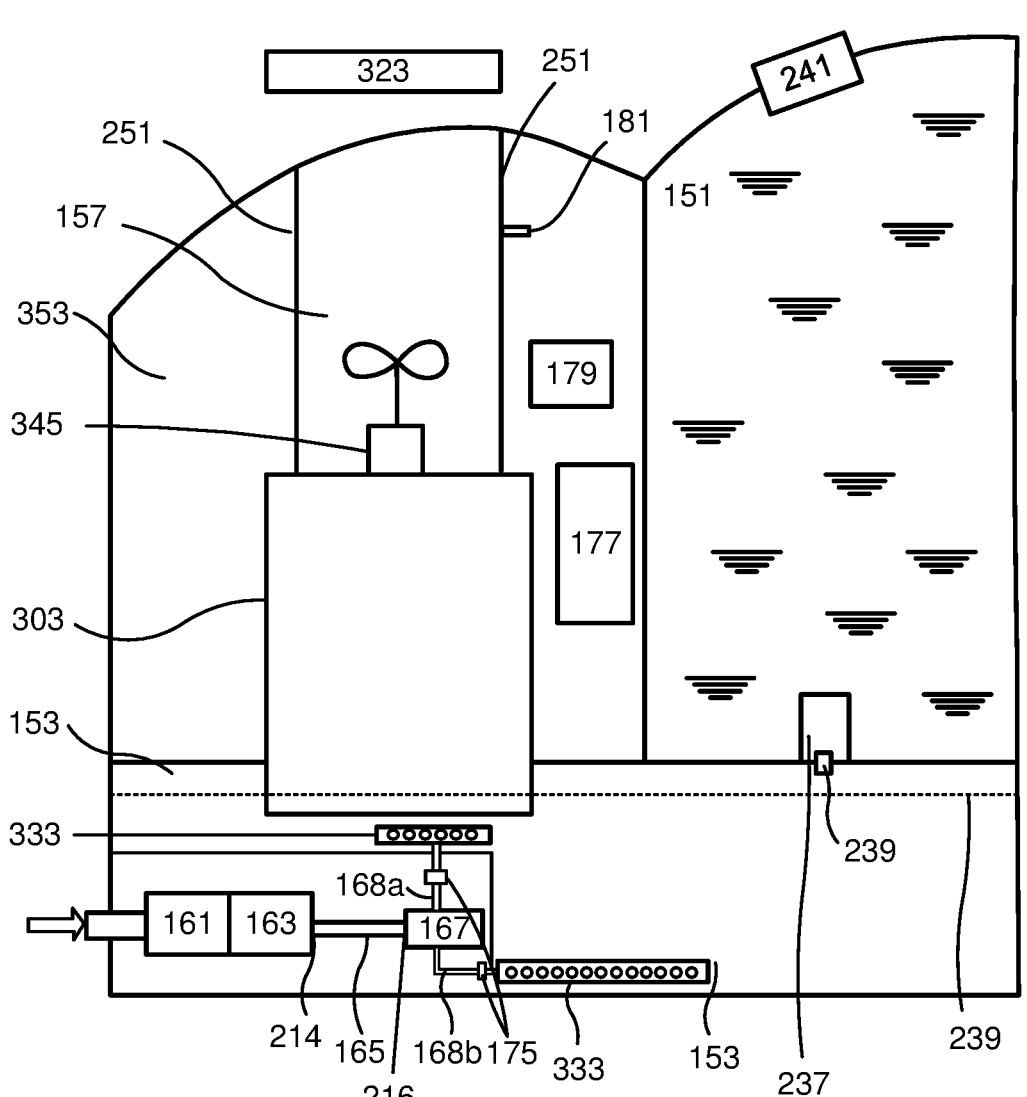
FIG. 16A is cross sectional diagram of one example of a self-sanitizing wick humidifier consistent with the present disclosure, with a filter in an open/uninstalled position.
Figure 16B:
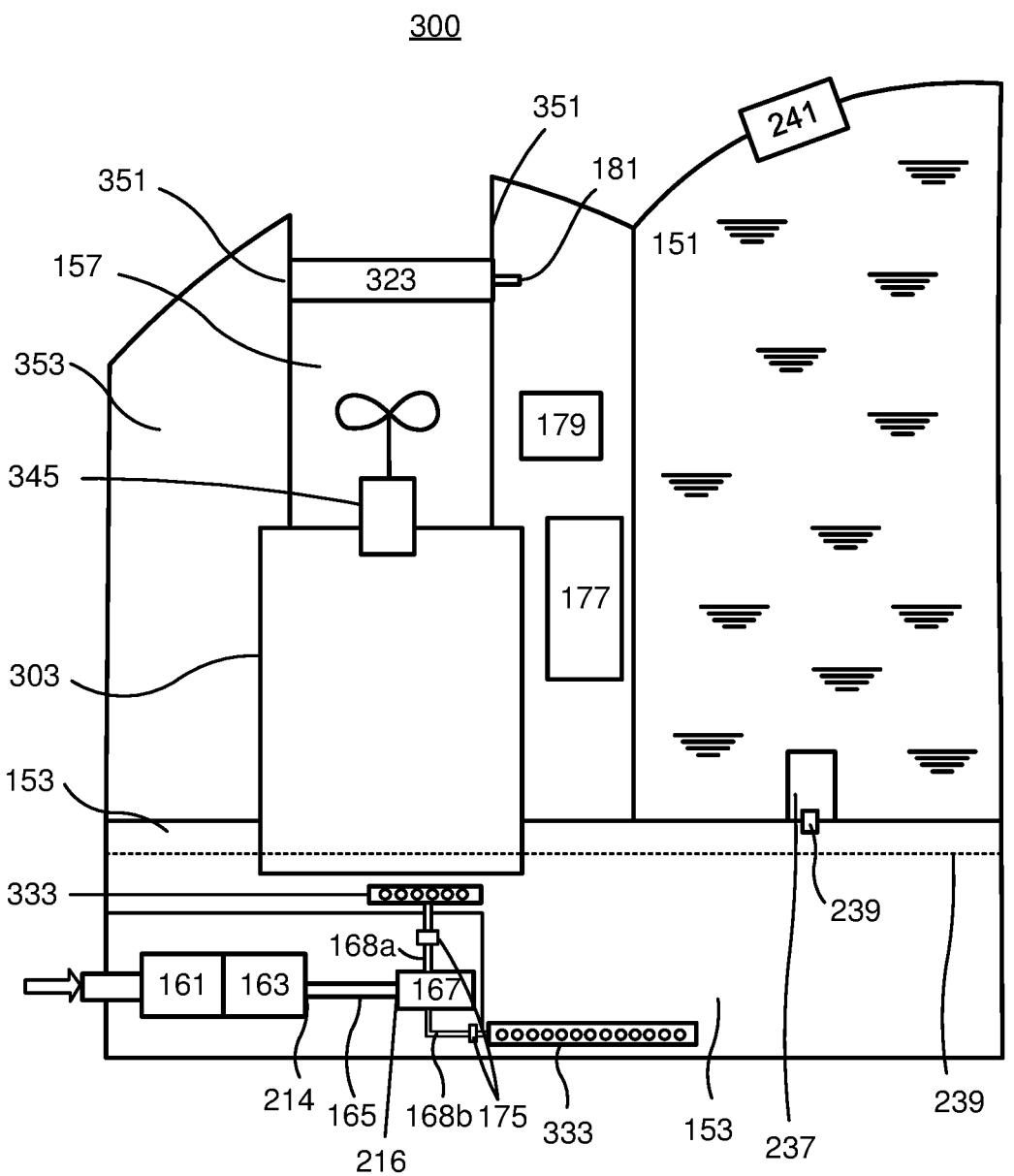
FIG. 16B is cross sectional diagram of the self-sanitizing wick humidifier of FIG. 16A, with the filter in a closed/installed position.

FIGS. 16A and 16B depict one example of a wick humidifier 300 consistent with the present disclosure. As shown, humidifier 300 includes many of the same or similar elements as humidifier 200 of FIGS. 15A and 15B. For example, humidifier 300 includes reservoir 151 (with an inlet 241, an outlet 239, and an optional demineralization cartridge 237), a base tray 153, mist channel 157, mist channel sidewall(s) 251, a sanitization system (including inlet fan/pump 161, sanitization gas generator 163, distribution line 165, distribution hub 167, first and second distribution channels 168a, 168b, controller 177, and filter sensor 181) as well as user interface 179. The nature and function of such elements is generally the same as described above in connection with FIGS. 15A and 15B and will not be reiterated in detail in the interest of brevity. Humidifier 300 differs from humidifier 200 in that it does not include a bottom chamber, it includes two diffusers 333 for base tray 153, it includes a wick 303 and a wick fan 345, and it includes a removable filter 323.

Like diffuser 233, diffusers 333 are generally configured to distribute sanitizing gas within base tray 153. Although two diffusers 333 are shown in the embodiment of FIGS. 16A and 16B, any suitable number of diffusers may be used. For example, one, two, three, four, five, or more diffusers may be used, and may be coupled to distribution hub 167 via a corresponding number of distribution channels 118. Alternatively, distribution hub 167, distribution channels, and diffusers 333 may be omitted, and distribution line may be fluidly coupled directly to base tray 153.

In some instances, a diffuser may be disposed within reservoir 151. For example, a flexible distribution channel may couple the diffuser to the sanitizing gas generator 163 such that the diffuser can be removably disposed within the reservoir 151.

Wick 303 is generally configured to draw in liquid (e.g. water) from base tray 153, and to facilitate the production of humidified air. In embodiments, wick 303 is a woven or non-woven fibrous mat that is configured to draw (e.g., via capillary action, adsorption, and/or absorption) liquid from base tray 153 above liquid level 239 and towards wick fan 345. During a humidification operation (e.g., initiated by user interface 179), wick fan 345 causes an airflow to flow over and/or through wick 303. As air passes over or through wick 303, at least a portion of the liquid on or within wick 303 evaporates into the air, resulting in the production of humidified air which is ultimately conveyed through mist channel 157 and into the environment.

Like filter 173, filter 323 is configured to absorb and/or convert a sanitizing gas to a breathable gas. In the embodiment of FIGS. 16A and 16B, however, filter 323 is not in the form of an electronically actuatable filter. Rather, filter 323 is configured to be manually installed and removed from mist channel 157. When filter 323 is removed (as shown in FIG. 16A), mist channel 157 is open and humidifier 300 is ready to perform a humidification operation. In contrast when filter 323 is installed (as shown in FIG. 16B), filter 323 blocks or substantially blocks mist channel 157. In the installed position, filter 323 may form a seal (e.g., a gas tight seal) with the sidewall(s) 251 of mist channel 157. In that regard, filter 323 may include one or more sealing elements (e.g., a peripheral seal) that engages and seals with the sidewall(s) 251 of mist channel 157. Alternatively or additionally, one or more sealing elements (not shown) may be disposed within mist channel 157 (e.g., within a groove formed within sidewall(s) 251), and are configured to engage and seal with an outward facing surface (e.g., a peripheral surface) of filter 323.

Upon initiation of a sanitization operation (e.g., via user interface 179), controller 177 may determine whether filter 323 is in the installed position, e.g., based at least in part on a filter sensor signal from sensor(s) 181. When controller 177 determines that filter 323 is not in the installed position, it may prevent the performance of the sanitization operation. When controller 177 determines that filter 323 is in the installed position, however, it may allow the sanitization operation to proceed.

During performance of the sanitization operation, inlet fan/pump 161 provides inlet air to sanitizing gas generator 163. Sanitizing gas generator 163 uses the inlet air to produce a sanitizing gas. The sanitizing gas flows into distribution line 165, distribution hub 167, first and second distribution channels 168a, 168b, and first and second diffusers 335. Sanitizing gas flows from the first and second diffusers 335 into the base tray 153, whereupon it will sanitize surfaces of the base tray, as well as any liquid/air therein. At least a portion of the sanitizing gas will flow from the base tray into a cavity containing wick 303 and towards mist channel 157. Sanitizing gas may flow from that cavity and/or the wick 303 into mist channel 157. Such flow of sanitizing gas may be facilitated by operation of wick fan 345, which may operate to draw sanitizing gas into mist channel 157. Sanitizing gas within mist channel 157 will sanitize surfaces 251 thereof. Ultimately at least a portion of the sanitizing gas will flow into filter 323, whereupon it will be absorbed and/or converted to breathable gas. As discussed above in connection with FIGS. 15A and 15B, controller 177 may determine the presence and/or concentration of sanitizing gas within humidifier 300 based at least in part on gas sensor signals provided by one or more sanitizing gas sensors (not shown). Controller 177 may compare a detected concentration of sanitizing gas to a threshold concentration and perform one or more safety operations when the detected concentration is greater than or equal to the threshold concentration, as discussed above.

Figure 18:
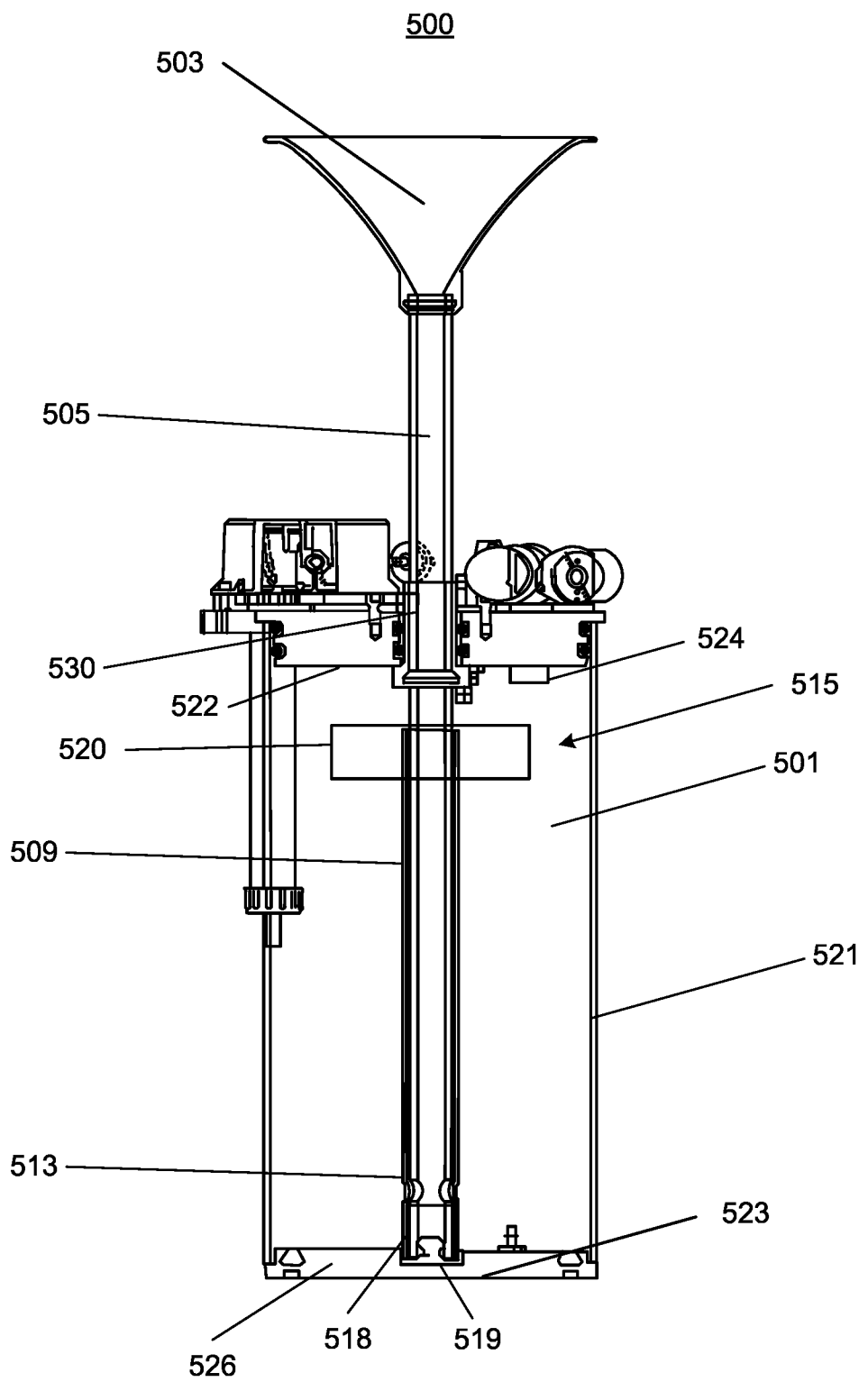
FIG. 18 is a cross sectional diagram of one example of a sanitizing system, including a float valve shutoff system, consistent with the present disclosure.

FIG. 18 depicts one embodiment of a humidifier 500 including a filling mechanism, additional details of which are shown in FIGS. 19-22. The humidifier 500 includes a reservoir 501 and a float valve 515 configured to prevent overfilling of the reservoir 501. The float valve 515 may be combined (in whole or in part) with any humidifier described herein such as, but not limited to, the humidifier 10, humidifier 150, humidifier 200, and/or humidifier 300, as well as any method described herein.

The float valve 515 may include an inner water inlet tube 505, an outer tube 509, a float 520 coupled to the outer tube 509, and optionally a flow blocker 518. The inner water inlet tube 505 may be coaxially aligned with the outer tube 509 (e.g., concentrically aligned) and is configured to receive water from an external source (e.g., faucet, picture, or the like). The inner water inlet tube 505 may be configured to be fluidly coupled to a funnel 503. For example, the funnel 503 may be removably fluidly coupled to the water inlet tube 505 or integrally coupled to the water inlet tube 505. The funnel 503 may facilitate pouring water into the inner water inlet tube 505. As explained herein, the float 520 is coupled to the outer tube 505 such that as the water level within the reservoir rises, the float 520 begins to rise with the water level causing the outer tube 505 to move (e.g., linearly) along the inner water inlet tube 505.

Figure 19:
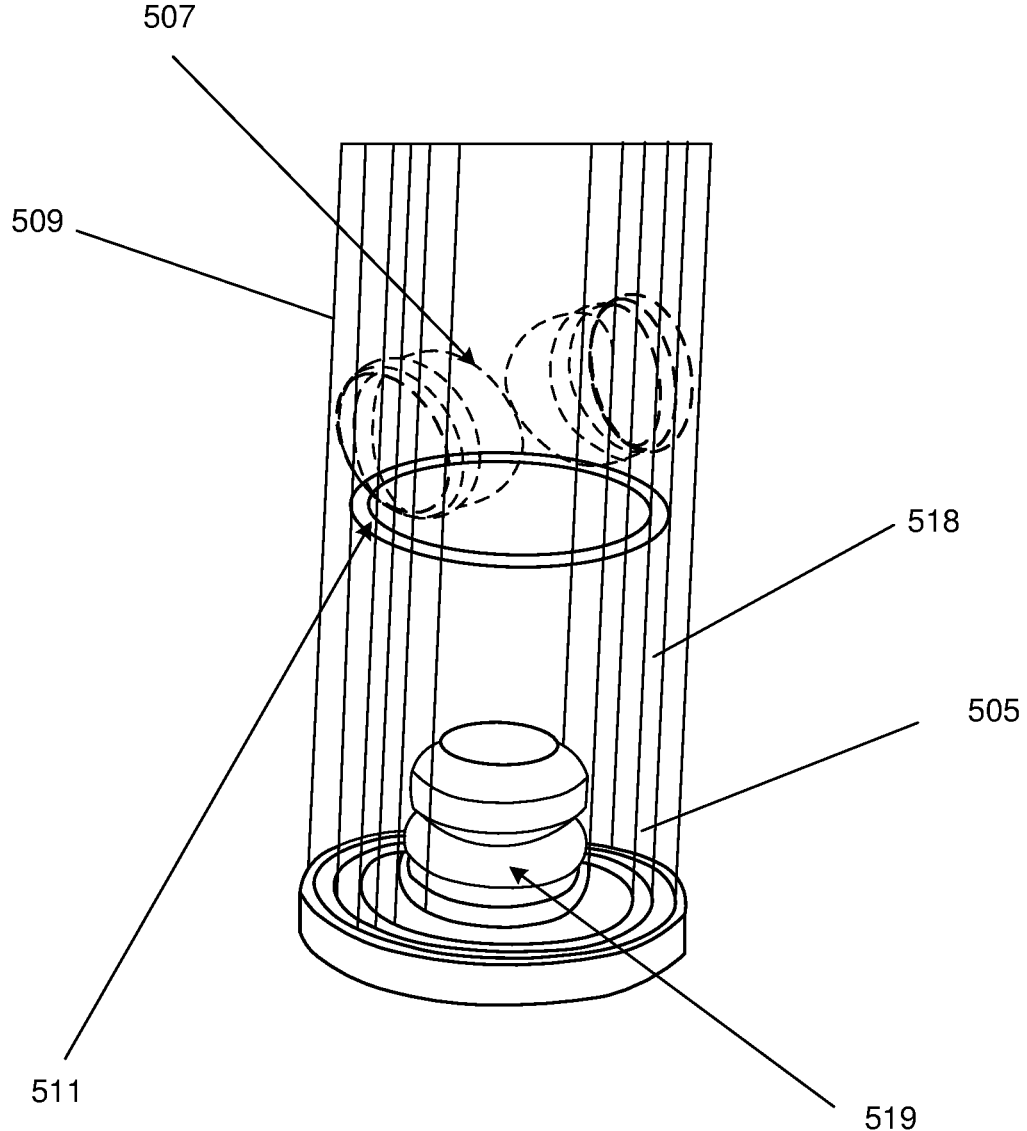
FIG. 19 generally illustrates one example of the float valve in an open position.
Figure 20:
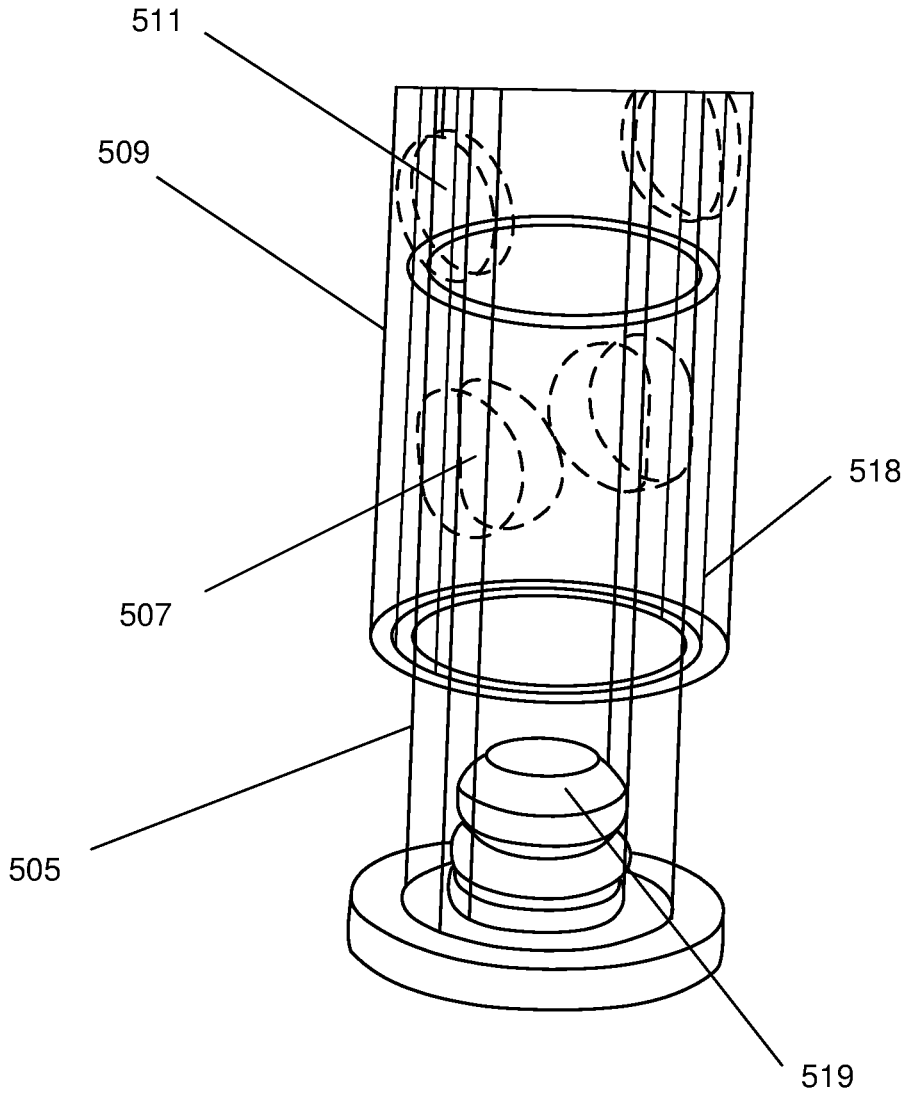
FIG. 20 generally illustrates one example of the float valve in a closed or sealed position.

With reference to FIGS. 18-20, when the water level within the reservoir 501 is below a predetermined fluid setpoint (e.g., a reservoir full setpoint), the float 520 is disposed in a first position (e.g., generally farthest away from the top 522 of the reservoir 501) and one or more outer holes 511 formed in the outer tube 509 are at least partially aligned with one or more inner holes 507 formed in the water inlet tube 505. When the outer holes 511 are aligned with the inner holes 507, water is able to flow from the water inlet tube 505, through the inner holes 507 and through the outer holes 511 of the outer tube 509 and into the reservoir 501.

Figures 21, 22:
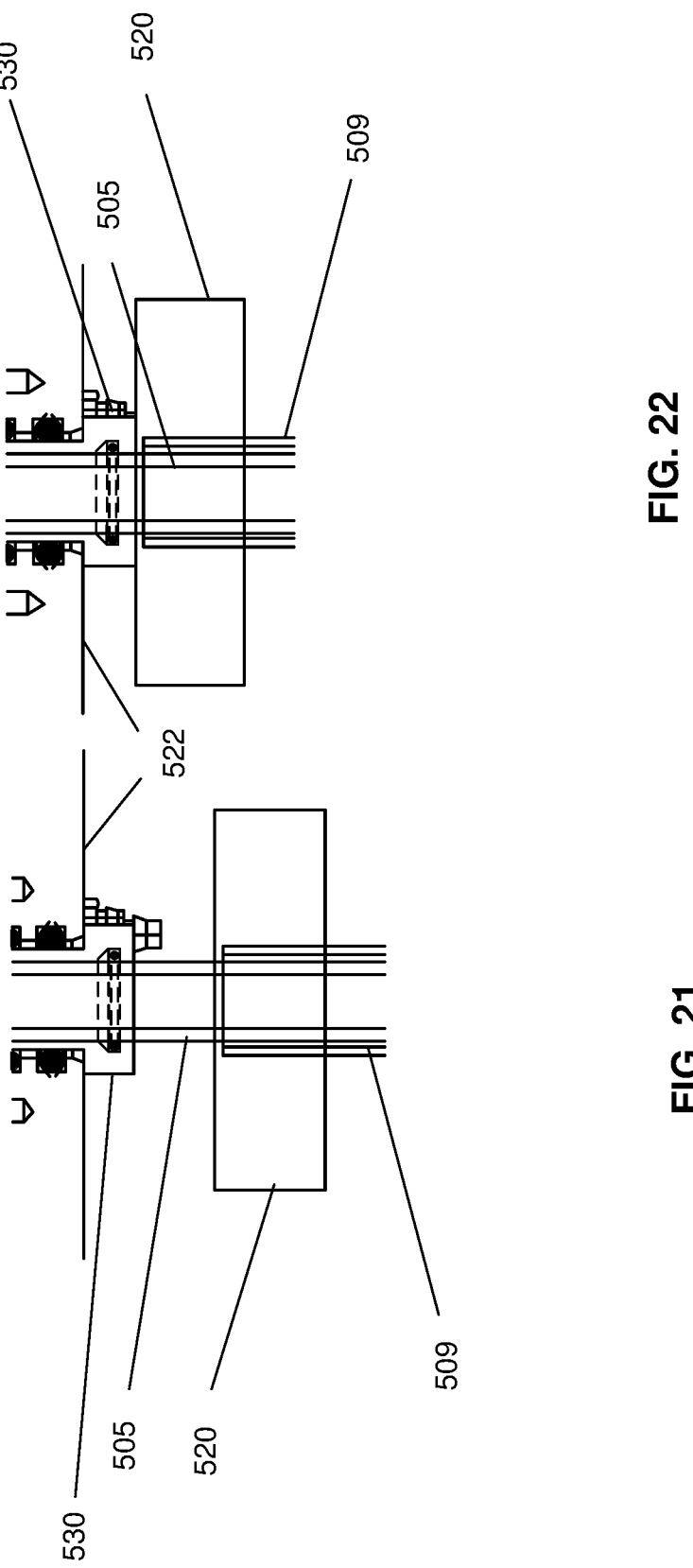
FIG. 21 generally illustrates one example of the float in an open position.
FIG. 22 generally illustrates one example of the float in a closed or sealed position.

As the water level within the reservoir 501 increases, the buoyancy of the float 520 causes the float 520 to rise which in turn causes the outer tube 509 to rise thereby changing the position of the outer tube 509 relative to the water inlet tube 505 and preventing further flow of water into the reservoir 501. With reference to FIG. 21, when the water level within the reservoir 501 reaches the predetermined fluid setpoint (e.g., a reservoir full setpoint), the one or more outer holes 511 of the outer tube 509 become misaligned with one or more inner holes 507 of the water inlet tube 505. According to at least one example, the misalignment of the inner holes 507 and outer holes 511 generally prevents water from flowing into the reservoir 501. Alternatively (or in addition), a flow blocker 518 may also be provided to generally prevent water from flowing into the reservoir 501. The flow blocker 518 may be coupled to or integrally formed from the outer tube 509. As the outer tube 509 moves upward due to the float 520, the flow blocker 518 may move over the inner holes 507 and generally seal the inner holes 507. The flow blocker 518 may include a thin tube, sheath, o-ring or the like that fits snugly around the water inlet tube 505 to generally seal the inner holes 507. Of course, the flow blocker 518 may include any configuration provided that it can extend over the inner holes 507 and generally seal the inner holes 507. It should be appreciated that the outer holes 509 may be eliminated and the float 520 may be coupled to the flow blocker 518 (e.g., by way of the outer tube 509) and the flow blocker 518 may selectively seal/unseal the inner holes 507. In such an example, the outer tube 509 may not be a tubular structure, but rather may include any configuration designed to couple the float 520 to the flow blocker 518 such that movement of the float 520 results in movement of the flow blocker 518.

When the float valve 515 closes, water can back up into the water inlet tube 505 (and optionally the funnel 503) indicating to the user that the reservoir 501 is filled. Additionally or alternatively, a sensor 524 may detect monitor the water level within the reservoir 501, the water inlet tube 505, the float 515 height, and/or the like, and alert the user when the reservoir 501 is full. It may be appreciated that the float 520 and/or flow blocker 518 may be disposed internally or externally to the water inlet tube 505. For example, if a seal were created by a flow blocker 518, that flow blocker 518 may be disposed within the water inlet tube 505 and in communication with the inner holes 507 of the water inlet tube 505.

In some embodiments the water inlet tube 505 has a cap or plug 519 that prevents water from flowing out of said end of the water inlet tube 505. In other embodiments, the cap 519 may be connected to the base 526 of the reservoir housing 501. In yet other embodiments, the water inlet tube 505 may be one piece with one or more permanently sealed ends that may or may not be affixed to the base of the reservoir housing 501.

As shown in FIG. 18, the float 520 may be substantially annular however, in unshown embodiments the float 520 may be cylindrical, cuboid, spherical, or some other geometric or nongeometric shape. Further, although the float 520 travels linearly in relation to the water inlet tube 505 and is attached directly to the outer tube 509, which acts as a sealing mechanism, other types of float valves may be used, such as a lever-type float valve (where the float moves in an arc shape in relation to the sealing mechanism). Further, the float valve may be replaced by a sensor (not shown) that seals the water inlet tube 505 by monitoring the water level, the float height, or some other factor.

Some embodiments include a spacer 530, such as the one in FIG. 18, that may interrupt or limit the movement of the float 520 at a desired level. The spacer 530 may be of any form including, but not limited to, a substantially lateral protrusion, a ring or circumferential protrusion, a free-floating spacer, or any other shape that creates sufficient space between the float 520 and a portion of the reservoir housing 501.

As shown in FIG. 18, the funnel 503 may be attached to the water inlet tube 505 by one or more o-rings, seals, or the like 517, e.g., around the outer diameter of the water inlet tube 505; however, other fastening means (e.g. threaded connection, press fit, clasps or clamps, etc.) may additionally or alternatively be used. In unshown embodiments, the funnel 503 may be permanently affixed to or continually formed with the water inlet tube 505, although it is understood that ease of disassembly is may be preferred.

Figure 17:
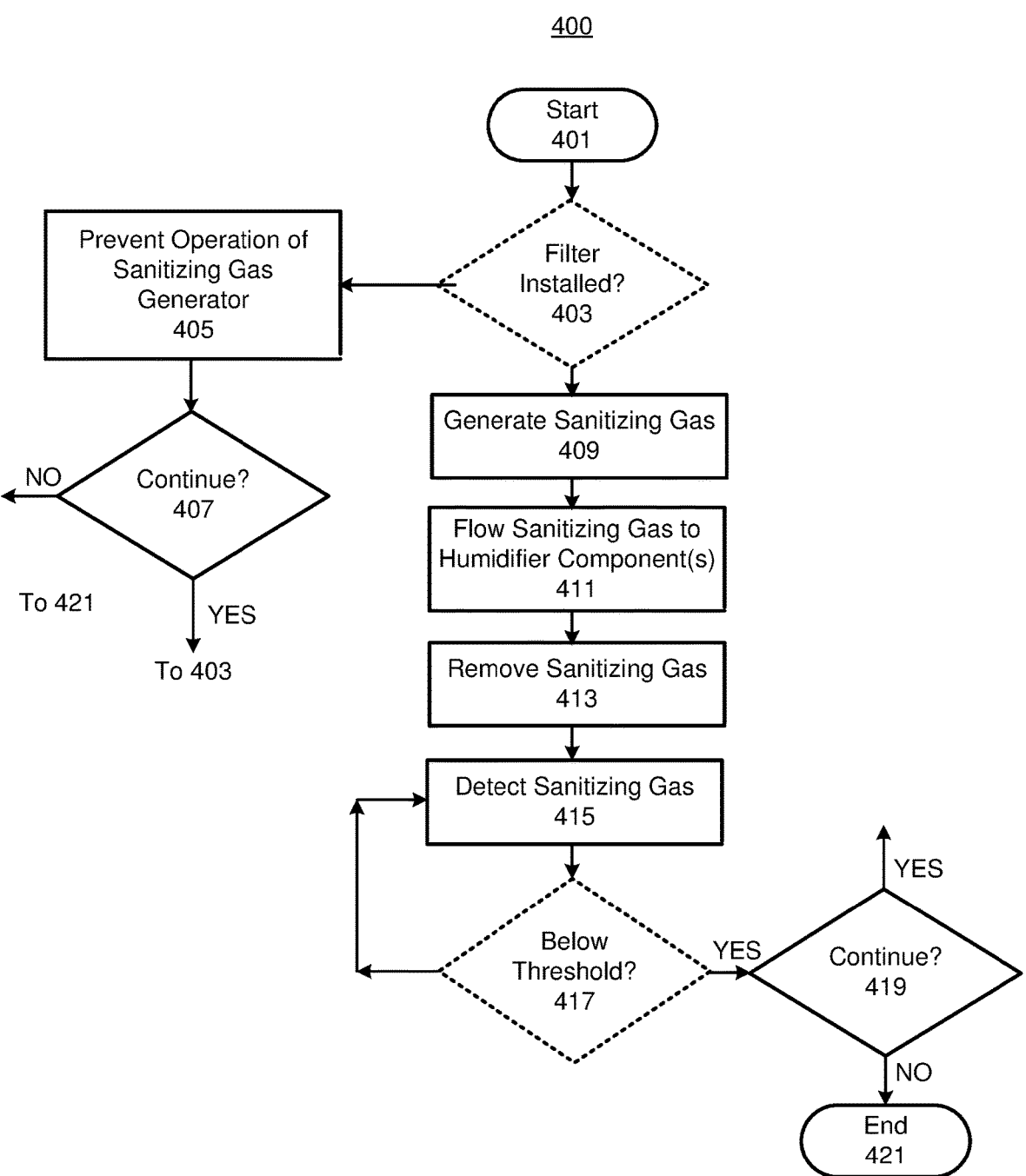
FIG. 17 is a flow chart of example operations of a humidifier sanitization method consistent with the present disclosure.

Another aspect of the present disclosure relates to methods of sanitizing a humidifier with a sanitizing gas. The method may used with, but is not limited to, any humidifier described herein. In that regard, reference is made to FIG. 17 which is a flow diagram of operations of one example of a method of sanitizing a humidifier consistent with present disclosure. As shown, method 400 begins with block 401. The method may then proceed to optional block 403, pursuant to which a determination may be made as to whether a filter is in an installed (e.g., closed) position. If not, the method may proceed to optional block 405, pursuant to which operation of a sanitizing gas generator in the humidifier may be prevented. The method may proceed from optional block 405 to optional block 407, pursuant to which a determination may be made as to whether the method is to continue. If so, the method loops back to optional block 403, but if not, the method proceeds to block 421 and ends.

If it is determined pursuant to block 403 that a filter is installed or if the operations of block 403 are omitted, the method may proceed to block 409. Pursuant to block 409, a sanitizing gas (e.g., ozone) may be generated, e.g., with a sanitizing gas generator. As discussed above, the sanitizing gas may be produced from or using inlet air from an inlet air pump/fan. The method may then proceed to block 411, pursuant to which sanitizing gas is flowed to one or more components of a humidifier.

For example and as discussed above, sanitizing gas may flow from the sanitizing gas generator into a distribution line. From the distribution line, the sanitizing gas may flow directly into one or more components of a humidifier (e.g., base tray, bottom chamber, reservoir, mist channel, etc.). Alternatively, sanitizing gas may flow from a distribution line into a distribution hub that is fluidly coupled to one or more distribution channels. From the distribution hub, the sanitizing gas may flow into the one or more distribution channels, and optionally into one or more diffusers disposed within one or more components of the humidifier.

The method may then proceed to block 413, pursuant to which sanitizing gas in the humidifier may be removed. In instances where the sanitizing gas is ozone, at least a portion of ozone gas introduced into the humidifier may convert to oxygen naturally over time. In any case, sanitizing gas may be removed by flowing it into and/or through a filter that is configured to absorb and/or convert the sanitizing gas into a breathable gas. Concurrent with or following block 413 the method may proceed to optional black 415—pursuant to which the presence and/or concentration of sanitizing gas may be detected. Consistent with the foregoing discussion, detection of the presence and/or concentration gas may be performed with one or more gas sensors and a controller. The gas sensors may provide a gas sensor signal to the controller, wherein the gas sensor signal is indicative of the presence and/or concentration of sanitizing gas within one or more components of a humidifier. The controller may determine whether sanitizing gas is presence and/or a detected concentration of sanitizing gas based at least in part on the sanitizing gas signal(s).

The method may then proceed to optional block 417, pursuant to which a determination may be made as to whether a detected concentration of sanitizing gas is below a threshold concentration. If not, the method may loop back to block 413 and removal of the sanitizing gas may be continued. If the detected concentration is below the threshold amount, however (or if optional blocks 415 and 417 are omitted), the method may proceed to block 419—pursuant to which a determination may be made as to whether the method is to continue. If so the method may loop back to block 409, but if not, the method may proceed to block 421 and end. The outcome of block 419 may be conditioned, for example, on whether a sanitization operation has been conducted for a pre-determined time.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A humidifier comprising:
a housing;
a water reservoir configured to hold a quantity of water;
a fan assembly configured to generate an air flow path within the humidifier;
a sanitizing system configured to generate a sanitizing gas and to transfer the sanitizing gas to the water reservoir such that at least a portion of the sanitizing gas is absorbed into the water in the water reservoir; and
a wick assembly fluidly configured to receive water from the water reservoir and transfer the water into the air flow path to generate humidified air, the wick assembly including a wick secured to a wick cartridge, a wick cover that extends over a top of the wick and includes a passage configured to allow a water inlet tube to extend through the wick assembly, and a wick air cavity at least partially defined as a volume between the wick cartridge, the wick, and the wick cover;
wherein the water received by the wick assembly includes at least a portion of the sanitizing gas absorbed into the water;
wherein at least a portion of the water received by wick assembly flows back to the water reservoir;
wherein a distal end of the water inlet tube is in fluid communication with the water reservoir;
wherein the fan assembly is configured to cause supply air to flow into the wick air cavity such that at least some of the supply air flow through and/or past the wick, and water from the water reservoir is transferred from the wick into the supply air to generate the humidified air.

2. The humidifier of claim 1, further comprising at least one water pump fluidly coupled to the water reservoir and to the wick assemble.

3. The humidifier of claim 2, further comprising a return water line configured to allow excess water to flow from the wick assemble back to the water reservoir.

4. A humidifier, comprising:
a housing;
a water reservoir configured to hold a quantity of water;
a fan assembly configured to generate an air flow path within the humidifier;
a sanitizing system configured to generate a sanitizing gas and to transfer the sanitizing gas to the water reservoir such that at least a portion of the sanitizing gas is absorbed into the water in the water reservoir; and a wick assembly fluidly configured to receive water from the water reservoir and transfer the water into the air flow path to generate humidified air, wherein the water received by the wick assembly includes at least a portion of the sanitizing gas absorbed into the water;
wherein at least a portion of the water received by wick assembly flows back to the water reservoir;
wherein the wick assembly includes a wick secured to a wick cartridge and wick air cavity, wherein the fan assembly is configured to cause supply air to flow into the wick air cavity such that at least some of the supply air flow through and/or past the wick, and water from the water reservoir is transferred from the wick into the supply air to generate the humidified air; and
wherein the wick includes a resiliently deformable material configured to be compressed within the wick cartridge.

5. The humidifier of claim 4, wherein the compression of the wick is configured to secure the wick to the wick cartridge.

6. A humidifier comprising:
a housing;
a water reservoir configured to hold a quantity of water;
a fan assembly configured to generate an air flow path within the humidifier;
a sanitizing system configured to generate a sanitizing gas and to transfer the sanitizing gas to the water reservoir such that at least a portion of the sanitizing gas is absorbed into the water in the water reservoir; and
a wick assembly fluidly configured to receive water from the water reservoir and transfer the water into the air flow path to generate humidified air, wherein the water received by the wick assembly includes at least a portion of the sanitizing gas absorbed into the water;
wherein at least a portion of the water received by wick assembly flows back to the water reservoir;
wherein the wick assembly includes a wick secured to a wick cartridge and wick air cavity, wherein the fan assembly is configured to cause supply air to flow into the wick air cavity such that at least some of the supply air flow through and/or past the wick, and water from the water reservoir is transferred from the wick into the supply air to generate the humidified air; and
wherein the wick cartridge includes a water tray, the water tray configured to be in fluid communication with the water reservoir and to hold a quantity of water therein such that the wick is in contact with water disposed within the water tray.

7. The humidifier of claim 6, wherein the water in the water tray includes a sanitizing gas to prevent and/or reduce the growth of bacteria, mold, and/or virus in the wick assembly.

8. The humidifier of claim 7, wherein the sanitizing gas in the water within the water tray breaks down while passing through the wick such that the humidified air will have a biologically inert amount of ozone.

9. The humidifier of claim 6, wherein the wick cartridge has a generally annular configuration such that the water tray extends generally circumferentially around the wick cartridge.

10. The humidifier of claim 6, wherein the water tray includes a base and an inner sidewall and outer sidewall extending from the base, and wherein supply air is configured to flow into the wick air cavity through one or more supply air wick cartridge inlets.

11. The humidifier of claim 9, wherein the wick cartridge includes one or more wick retention protrusions extending from the inner or outer sidewalls, the one or more wick retention protrusions configured to secure the wick to the wick cartridge and to position the wick such that the wick is at least partially disposed within the water tray.

12. The humidifier of claim 10, wherein the one or more wick retention protrusions extend radially inward from the outer sidewall.

13. The humidifier of claim 9, wherein the water tray includes a divider wall, the divider wall extending from the base between the inner and outer sidewalls.

14. The humidifier of claim 11, wherein the wick cartridge further includes a water inlet port disposed proximate to one side of the divider wall.

15. The humidifier of claim 13, wherein the wick cartridge further includes one or more water outlet ports disposed on the opposite side of the divider wall, wherein water pumped to the water tray may enter the water tray proximate one side of the divider wall through the water inlet port, flow around the water tray to the opposite side of the divider wall, and drain out of the water tray through the water outlet ports back to the water reservoir.

16. The humidifier of claim 15, wherein the wick cartridge further includes at least one air bleed port, the air bleed port configured to allow air within the water tray to be removed from the water tray as water is pumped into the water tray.

17. The humidifier of claim 15, wherein the opening to the one or more water outlet ports is selected such that the air bleed port is partially submerged in the water within the water tray but water does not flow out of the air bleed port.

\*   \*   \*   \*   \*